United States Patent [19]
Garnier et al.

[11] Patent Number: 6,054,269
[45] Date of Patent: Apr. 25, 2000

[54] POLYNUCLEOTIDES AND THEIR USE FOR DETECTING ENTEROCOCCI AND STREPTOCOCCI BACTERIAL STRAINS

[75] Inventors: Fabien Garnier, Paris; Guy Gerbaud, Saint-Maur-des-Fosses; Marc Galimand; Patrice Courvalin, both of Paris; Sylvie Dukta-Malen, Fresnes; Murielle Charles, Romainville, all of France; Stefan Evers, Mullheim, Germany; Barbara Casadewall, Fleurance, France

[73] Assignee: Institut Pasteur, Paris, France

[21] Appl. No.: 08/882,501

[22] Filed: Jun. 25, 1997

[51] Int. Cl.$^7$ .............................. C12Q 1/68; C12P 19/34; C07H 21/04; C07H 21/02
[52] U.S. Cl. ........................... 435/6; 435/91.1; 435/91.2; 536/23.1; 536/24.3; 536/24.31; 536/24.32; 536/24.33
[58] Field of Search ............................ 435/6, 91.1, 91.2; 536/23.1, 24.3, 24.31, 24.32, 24.37

[56] References Cited

FOREIGN PATENT DOCUMENTS

WO 88/03957  6/1988  WIPO.

OTHER PUBLICATIONS

Garnier et al, Genbank records SMU69164, SMU69165, SSU69167, SSU69168, SOU69166, SGU69163, Feb. 1997.
Dutka–Malen et al, "Sequence of the vanC gene of *Entetrococcus gallinarum* BM4174 encoding a D–alanine:D–alanine ligase related protein necessary for vancomycin resistance", Gene 112:53–58, 1992.
Kajimura et al, "Application of long synthetic oligonucleotides for gene analysis: effect of probe length and stringency conditions on hybridization", GATA 7(4):71–79, Aug. 1990.
Navarro et al, "Analysis of genes encoding a D–alanine–D–alanine ligase related enzymes in *Entterococcus casseliflavus* and *Enterococcus flavescens*", Antimicrobial Agents and Chemotherapy 38(8):1788–1793, Aug. 1994.
Evers et al, "Sequence of the vanB and ddl genes encoding D–alanine:D–lactate and D–alanine:D–alanine ligases in vancomycin resistant *enterococcus faecalis* V583", Gene 140:97–102, 1994.
Evers et al, "Evolution of structure and substrate specificity in D–alanine:D–alanine ligases and related enzymes", J. Mol. Evolution 42(6):706–12 Abstract Only, Jun. 1996.
Invitrogen catalog, p. 35, 1992.
Stratagen catalog, p. 39, 1988.
Garnier et al, "Identification of clinically relevant viridans group streptococci to the species level by PCR", J. Clin. Microbiol. 35(9):2337–2341, Sep. 1997.

*Primary Examiner*—Jeffrey Fredman
*Attorney, Agent, or Firm*—Finnegan, Henderson, Farabow, Garrett & Dunner, L.L.P.

[57] ABSTRACT

Polynucleotides and oligonucleotides for identification of species of the Streptococcus genus and the Enterococcus genus are provided. The polynucleotides and oligonucleotides are useful as probes and primers. Polypeptides expressed by the polynucleotides and oligonucleotides are useful for the preparation of monoclonal and polyclonal antibodies that recognize the polypeptides.

69 Claims, 9 Drawing Sheets

```
                                    1                                                      50
SEQ ID NO. 21  S. gordonii       TTCCTAGAAG TCCTCAAAAT GCCTTATGTC GGCTGTAATA TTCTATCTTC
SEQ ID NO. 22  S. sanguis        TTCCTAGAAG TGCTCAAAAT GCCTTATGTC GGCTGTAATA TTTTATCTTC
SEQ ID NO. 17  S. mitis          TTCCTTGAAG TTTTGAAAAT GCCTTATGTT GGTTGCAACA TTTTGTCATC
SEQ ID NO. 19  S. oralis         TTTCTTGAAG TTTTGAAAAT GCCTTATGTC GGCTGCAATA TCCTGTCATC
SEQ ID NO. 23  S. anginosus      TTTCTTGAAG TGTTGAAAAT GCCTTATGTG GGTTGCAATA TCCTTTCTTC
SEQ ID NO. 24  S. constellatus   TTTCTTGAAG TGTTGAAAAT GCCTTATGTG GGTTGTAATA TCCTTTCTTC
SEQ ID NO. 25  S. intermedius    TTTCTTGAAG TGTTGAAAAT GCCTTATGTT GGCTGCAATA TTCTTTCGTC
SEQ ID NO. 20  S. salivarius     TTCCTCGAAA CCCTCAAATT GCCATATGTG GGTACTAATG TTCTTTCTTC
SEQ ID NO. 18  S. mutans         TTTCTTGAAG TTTTAAAAAT GCCTTATGTG GGAACCAATA TTCTGTCATC
                                 ** ** ***     *  ****  *** ******    **  **   *  ** **

51                                                    100
               S. gordonii       TAGCCTGGCC ATGGATAAAA TTACGACCAA GCGAGTTCTG GAATCAG....
               S. sanguis        TAGCTTAGCC ATGGATAAAA TCACGACCAA GCGAGTGCTG GAATCAG....
               S. mitis          TAGCCTTGCC ATGGATAAAA TCACGACCAA GCGTGTGTTA GAATCTG....
               S. oralis         AAGTCTTGCC ATGGATAAAA TCACGACCAA GCGTGTTTTA GAATCTG....
               S. anginosus      TAGTGTTGCT ATGGACAAAA TCACGACAAA ACGAGTGTTA GCTTCTG....
               S. constellatus   TAGTGTTGCC ATGGACAAAA TCACAACAAA ACGAGTGTTA GCTTCTG....
               S. intermedius    GAGTATTGCG ATGGATAAAA TCACAACTAA ACGTGTGTTA GCTTCTG....
               S. salivarius     AAGTGTGGCT ATGGACAAGA TTATGACCAA GCATATTCTT GAAGTTG....
               S. mutans         TAGTGTAGCT ATGGATAAGA TTACAACAAA GCAAGTTTTA GAAAGTGCGA
                                  ** * **   ***** ** *  **  *        *     *    *     *
```

FIG. 1A

```
          101                                                          150
S. gordonii      CAGGTATTGC TCAAGTACCT TATGTAGCGG TGGTTGATGG TGAGGATCTA
S. sanguis       CAGGAATAGC CCAAGTGCCT TATGTGGCGC TGGTCGATGG CGAGGATCTA
S. mitis         TCGGGATTGC CCAAGTTCCT TATGTGGCCA TTGTCGAAGG TGATGATATG
S. oralis        TAGGGATTGC CCAAGTACCT TATGTGGCTA TCGTCGAAGG TGATGATGTG
S. anginosus     CTGGCATTCC GCAAGTTCCC TATGTAGCAG TGATTGAAGG GGAAAATATA
S. constellatus  CTGGCATTCC GCAAGTTCCC TATGTAGCAG TGATTGAAGG GGAAAATATA
S. intermedius   CTGGTATTCC TCAAGTACCG TATGTAGCCG TAGTGGAAGG GGAAGATGTA
S. salivarius    CTGGTGTGCC TCAGGTTGCC TATACAGTCT TCATCGAGGG TGAAGATTTG
S. mutans        CTACTATTCC TCAAGTAGCT TATGTTGCTC TTATTGAAGG CGAGCCTTTA
                   *   *  ** **  *   *   * *     *   *  * ***         * *

151                                                          200
S. gordonii      GAGCAAAAAA TCCAGGAAAT TGAAGAGAAA CTGTCCTATC CCGTCTTCAC
S. sanguis       GAGCAAAAAA TCCAAGAAAT CGAGGAGAAA TTGACCTATC CAGTCTTCAC
S. mitis         ACTGCTAAAA TTGCTGAAGT TGAAGAAAAA TTGACTTATC CAGTTTTCAC
S. oralis        ACTGCTAAAA TAGCTGAAGT TGAAGAAAAA TTGACTTATC CAGTCTTCAC
S. anginosus     GACGAAAAGA TTGCAGAAGT AGAAGCCAAT CTGACTTATC CAGTCTTCAC
S. constellatus  GACGAAAAGA TTGCAGAAGT AGAAGCCAAT CTAACTTATC CAGTTTTTAC
S. intermedius   GAAGAAAAGA TTGCAGAAGT AGAAGTTAAT CTGACTTATC CAGTCTTTAC
S. salivarius    GAAGCAGCAG TAGCAGAGAC GCTTGAAAAA TTGACCTTCC CAGTCTTTGT
S. mutans        GAAAGCAAGT TGGCAGAAGT TGAAGAGAAA TTGATTTATC CTGTATTTGT
                   *         *             *  *         *    * *    * ***
```

FIG. 1B

|  | 201 |  |  |  |  | 250 |
|---|---|---|---|---|---|---|
| S. gordonii | CAAACCTTCT | AATATGGGCT | CCAGTGTCGG | CATTTCAAAA | TCTGATAATC |
| S. sanguis | CAAACCTTCT | AATATGGGCT | CCAGTGTCGG | CATTTCTAAA | TCGGA.GACC |
| S. mitis | AAAACCATCT | AACATGGGCT | CTAGTGTCGG | TATTTCTAAG | TCTGAAAATC |
| S. oralis | GAAGCCGTCA | AACATGGGTT | CAAGTGTCGG | TATTTCTAAG | TCTGAAAACC |
| S. anginosus | AAAACCGTCA | AATATGGGAT | CTAGTGTCGG | CATTTCTAAG | TCTGAAAATC |
| S. constellatus | AAAACCGTCA | AATATGGGCT | CTAGTGTCGG | CATTTCTAAG | TCTGAAAATC |
| S. intermedius | TAAACCATCA | AATATGGGCT | CTAGTGTTGG | CATTTCTAAA | TCTGAAAACA |
| S. salivarius | CAAACCTGCT | AATATGGGGT | CATCTGTTGG | GATTTCTAAA | GCTGAAAATG |
| S. mutans | TAAGCCAGCT | AATATGGGGT | CTAGTGTTGG | TATTTCTAAA | GCAGAAAATC |
|  | ** * | ** ***** | ** * | **** * | * ** |

|  | 251 |  |  |  |  | 300 |
|---|---|---|---|---|---|---|
| S. gordonii | AGGAAGAACT | GCGTGCTTCT | CTGGACCTGG | CTTTCAAATA | CGATAGTCGG |
| S. sanguis | AAGCAGAACT | GCGTGCTTCT | CTGGACCTGG | CTTTCAA..T | ACGACGCCGA |
| S. mitis | AAGAGAAACT | TCGTCAAGCC | TTGAAACTTG | CCTTCCAATA | TGATAGCCGT |
| S. oralis | AAGAGGAACT | CCGTCAAGCT | TTGGAACTTG | CCTTCCAATA | TGACAGCCGT |
| S. anginosus | AAGATGAATT | GCGCTCTGCT | CTTGAAGCT | CTTTCAAATA | TGATAGCCGT |
| S. constellatus | AAGATGAATT | GCGTTCTGCT | CTTGAATTGG | CTTTCTAAAT | TGATAGCCGT |
| S. intermedius | AAGATGAATT | GTGTTCTGCT | CTTAAGTTAG | CTTTAAATA | CGATACCCGT |
| S. salivarius | AAGCAGAGCT | TCGTGCAGCG | ATTGATCTGG | CTCTCAAATA | TGATAGCCGT |
| S. mutans | GCACTGACTT | AAAACAAGCT | ATTGCACTTG | CTTGAAGTA | TGACAGTCGT |
|  | * * | * * | * * | * * | ** |

FIG. 1C

```
              301                                                                           350
S. gordonii      GTACTAGTCG AGCAAGG... TGTAACAGCT CGTGAGATTG AGGTTGGACT
S. sanguis       GTACTGGTTG AGCAAGGAGA TCGAACGGCT CGCGAGATTG AGGTTGGGCT
S. mitis         GTCTTGGTTG AACAAGG... GGTAAATGCC CGTGAAATGC AGGTTGGCCT
S. oralis        GTCTTGGTAG AGCAAGG... GGTGAATGCC CGTGAAATCG AGGTTGGTCT
S. anginosus     GTCTTGATTG AGCAAGG... TGTCAATGCG CGTGAAATTG AAGTTGGTTT
S. constellatus  GTCTTGATTG AGCAAGG... TGTCAATGCG CGTGAAATTG AAGTTGGTTT
S. intermedius   GTCTTGATTG AGCAAGG... TGTCAATGCG CGTGAAATCG AGGTTGGTTT
S. salivarius    ATCTTGATTG AGCAAGG... TGTGGTTGCC CGTGAAATTG AGGTTGGTTT
S. mutans        GTTTTAATTG AACAAGG... TGTGGATGCG CGTGAGATTG AGGTTGGTAT
                  *  * * **   ******    **         **     *     * *****

351                                                                           400
S. gordonii      TCTTGGTAAC ACTGATGTCA AAAGCAGTCT TCCAGGGGAA GTTGTTAAGG
S. sanguis       TTTTGGGCAAT GTTGACGTCA AGAGTACCCT ACCTGGAGAA GTGGTCAAGG
S. mitis         ACTGGGTAAC TACGATGTTA AAAGCACGCT TCCAGGAGAA GTAGTTAAGG
S. oralis        CTTGGGCAAC TACGATGTGA AGAGCACGCT TCCTGGTGAA GTGGTCAAGG
S. anginosus     ACTTGGAAAT GAAGGAGCCA AAAGCAGTTT GCCAGGTGAG GTAGTGAAAG
S. constellatus  ACTTGGAAAT GAAGGAGCCA AAAGCAGTTG GCCAGGTGAG GTAGTGAAAG
S. intermedius   ATTTGGAACA GAAGGAGCTA AAAGTAGTTT ACCAGGTGAA GTGGTGAAAG
S. salivarius    CCTTGGCAAT ACGACTGTCA AAACGACTAA TCCAGGTGAA GTAGTCAAAG
S. mutans        TTTAGGAAAT ACTGATGTTA AAACAACTTT ACCGGGAGAG ATTGTCAAAG
                  *  *          * *            *     *  * **     ** *****
```

FIG. 1D

|   | 401 |   |   |   |   | 450 |
|---|---|---|---|---|---|---|
| S. gordonii | ATGTGGCTTT | CTATGATTAT | CAAGCCAAAT | ATATTGACAA | TAAAATCACC |
| S. sanguis | ACGTGGCTTT | TTATGACTAT | GAAGCCAAAT | ACATTGATAA | TAAAATTACC |
| S. mitis | ATGTGCCTT | TTATGACTAT | GATGCCAAGT | ATATTGACAA | CAAGATTACC |
| S. oralis | ATGTTGCCTT | TTATGACTAT | GATGCCAAGT | ATATTGACAA | CAAGATTACC |
| S. anginosus | ATGTTGCTTT | CTATGACTAC | GAAGCCAAGT | ACATTGACAA | CAAAATCACC |
| S. constellatus | ATGTTGCTTT | CTATGACTAC | GAAGCCAAGT | ACATTGACAA | CAAAATCACC |
| S. intermedius | ATGTCGCTTT | TTATGATTAC | GAAGCCAAGT | ACATTGACAA | TAAAATTACT |
| S. salivarius | ATGTGGCTTT | CTATGACTAT | CAAGCCAAGT | ACATTGACAA | TAAGATTACC |
| S. mutans | TTGTGGCTTT | TTATGATTAC | GAAGCCAAGT | ATATTGATAA | TAAGATCACC |
|   | ** * ** | ***** ** | * ***** | * ****** | ** ** |

|   | 451 |   |   |   |   | 500 |
|---|---|---|---|---|---|---|
| S. gordonii | ATGGCAATCC | CAGCTCAGCT | TCCTGAAGGT | GTTGTGAATA | CTATGCGTCA |
| S. sanguis | ATGGATATTC | CGGCCAAGAT | TCCAGAAGAA | GTGGTGAGTC | TGATGCGTCA |
| S. mitis | ATGGATATCC | CAGCTAAAAT | CAGTGATGAT | GTGGTAGCTG | TCATGCGTCA |
| S. oralis | ATGGACATCC | CAGCCAAGAT | TAGTGATGAT | GTAGTAGCTG | TCATGCGTCA |
| S. anginosus | ATAGATATTC | CTGCAAAACT | CTCTGAAGAT | GTCATTGCCA | CTATGCGTCA |
| S. constellatus | ATGGATATTC | CTGCAAAACT | CTCTGAAGAT | GTCATTGTCA | CTATGCGGCA |
| S. intermedius | ATGGATATTC | CTGCAAAAAT | CTCTGAAGAT | GTCATTGTCA | CTATGCGGCA |
| S. salivarius | ATGGACATCC | CAGCTCACGT | TCCTGCAGAA | GTTATTGCCA | CTATGTGTGT |
| S. mutans | ATGGCTATTC | CGGCAGAAAT | AGATCCTGTT | ATCGTTGAAA | AAATGCGGGA |
|   | ** * * | * | * | * * | *** * |

FIG. 1E

```
              501                                                              550
S. gordonii   AAATGCCGAG ACAGCTTTTC GTGCTATTGG TGGGTTAGGA CTATCTCGCT
S. sanguis    AAATGCAGAG GCAGCTTTCC GAGCTCTGGG CGTCTGGGG  CTGTCCCGTT
S. mitis      GAATGCAGAA ACTGCCTTCC GTGCTATTGG TGGTTTAGGT CTATCTCGTT
S. oralis     TAATGCAGAA ACTGCCTTCC GTGCGATCGG TGGCCTCGGT CTGTCTCGTT
S. anginosus  ATATGCTGAA AAACGATTCC ATGCTATTGG TGGCCTGTGGT TTAGCTCGCT
S. constellatus ATATGCAGAA AAAGCTTTCC ATGCTATTGG CGGTGTTGGT TTAGCTCGCT
S. intermedius CTATGCTGAA AAAGCTTTCC ATGCAATTGG TGGCGTTGGG TTATCTCGTT
S. salivarius CTATGCGGGCC AAGGCCTTCC GTGCCCTCGG TGGTGTGGT  CTTGCCCGCT
S. mutans     TTATCGTGCA ACAGCTTTCC GAACTTTGGG CTGCTGTGGA CTTTCTCGCT
              *    * * *          * *   * *   *   * * * * *  * * * * * *

551                                                              597
S. gordonii   GTGATTTTTT CTACACAGAA GATGGTCAGG TCTTTCTTAA TGAGCTC
S. sanguis    GTGATTTCTT CTATGCAGAA GATGGTCAGG TCTTCCTTAA TGAGCTC
S. mitis      GTGATTTCTT CTATACAGAA AAGGGAGAGA TTTTCCTAAA CGAGCTC
S. oralis     GTGATTTCTT CTATACAGAT AAGGGCGAGA TTTTCCTAAA CGAGCTT
S. anginosus  GCGATTTCTT TTATACTGAT AAGGGCGAGA TTTTCCTAAA TGAGTTA
S. constellatus GCGATTTCTT TTATACTGAT AAGGGCGAGA TTTTCCTTAA TGAGTTA
S. intermedius GTGATTTCTT TTATACTAAT AAGGGTGAGA TTTTCCTCAA TGAGTTA
S. salivarius GTGATTTCTT CCTGACAGAG GATGGAGCCA TCTACCTTAA CGAGCTC
S. mutans     GTGATTTCTT CCTAACAGAG GATGGGAAAG TTTATTTGAA TGAACTC
              * ****** *   *       *     *   *      * *     * *
```

FIG. 1F

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 20 base pairs (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:1:

GTCGAAGGTG ATGATATGAC                                            20

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:2:

CTGCATTCTG ACGCATGACA G                                          21

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

ATTGAAGGCG AGCCTTTAGA AAG                                        23

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

CAACGATAAC AGGATC                                                16

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

TGCAGAAGTA GAGGCAAATC                                            20

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

GCCAACTGCT TTTGGCTCCT T                                                    21

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:7:

GCAGCAGTAG CAGAGACGCT                                                      20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:8:

GTCATGACTT CTGCAGGCAC                                                      20

(2) INFORMATION FOR SEQ ID NO:9:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:9:

GTCGATGGCG AGGATCTAGA GC                                                   22

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:10:

ACCTCAATCT CGCGAGCCGT                                                      20

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:11:

```
TGAAATCGAG GTTGGCCTAC                                                    20

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

CGTTTAGGAA AATCTCKCCC TT                                                 22

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

CTTATGTCGG CTGCAATATC C                                                  21

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

GTCGATGGCG AGGATCTAGA GC                                                 22

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

AACAACTTCC CCTGGAAGAC                                                    20

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

CTCTGCATTT TGACGCATCA G                                                  21

(2) INFORMATION FOR SEQ ID NO:17:
```

(i) SEQUENCE CHARACTERISTICS:
    (A) LENGTH: 591 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Streptococcus mitis (xi) SEQUENCE DESCRIPTION: SEQ ID NO:17:

```
TTCCTTGAAG TTTTGAAAAT GCCTTATGTT GGTTGCAACA TTTTGTCATC TAGCCTTGCC      60
ATGGACAAAA TCACGACCAA GCGTGTGTTA GAATCTGTCG GGATTGCCCA AGTTCCTTAT     120
GTGGCCATTG TCGAAGGTGA TGATATGACT GCTAAAATTG CTGAAGTTGA AGAAAAATTG     180
ACTTATCCAG TTTTCACAAA ACCATCTAAC ATGGGTTCTA GTGTCGGTAT TTCTAAGTCT     240
GAAAATCAAG AGGAACTTCG TCAAGCCTTG AAACTTGCCT TCCAATATGA TAGCCGTGTC     300
TTGGTTGAAC AAGGGGTAAA TGCCCGTGAA ATCGAGGTTG GCCTACTGGG TAACTACGAT     360
GTTAAAAGCA CGCTTCCAGG AGAAGTAGTT AAGGATGTTG CCTTTTATGA CTATGATGCC     420
AAGTATATTG ATAACAAGAT TACCATGGAT ATCCCAGCTA AAATCAGTGA TGATGTGGTA     480
GCTGTCATGC GTCAGAATGC AGAAACTGCC TTCCGTGCTA TTGGTGGTTT AGGTCTATCT     540
CGTTGTGATT TCTTCTATAC AGATAAGGGA GAGATTTTCC TAAACGAGCT C              591
```

(2) INFORMATION FOR SEQ ID NO:18:

(i) SEQUENCE CHARACTERISTICS:
        (A) LENGTH: 594 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus mutans (xi) SEQUENCE DESCRIPTION: SEQ ID NO:18:

```
TTTCTTGAAG TTTTAAAAAT GCCTTATGTG GGAACCAATA TTCTGTCATC TAGTGTAGCT      60
ATGGATAAGA TTACAACAAA GCAAGTTTTA GAAAGTGCGA CTACTATTCC TCAAGTAGCT     120
TATGTTGCTC TTATTGAAGG CGAGCCTTTA GAAAGCAAGT TGGCAGAAGT TGAAGAGAAA     180
TTGATTTATC CTGTATTTGT TAAGCCAGCT AATATGGGTT CTAGTGTTGG TATTTCTAAA     240
GCAGAAAATC GCACTGACTT AAAACAAGCT ATTGCACTTG CTTTGAAGTA TGACAGTCGT     300
GTTTTAATTG AACAAGGTGT GGATGCGCGT GAGATTGAGG TTGGTATTTT AGGAAATACT     360
GATGTTAAAA CAACTTTACC GGGAGAGATT GTCAAAGTTG TGGCTTTTTA TGATTACGAA     420
GCCAAGTATA TTGATAATAA GATCACCATG GCTATTCCGG CAGAAATAGA TCCTGTTATC     480
GTTGAAAAAA TGCGGGATTA TCGTGCAACA GCTTTCCGAA CTTTGGGCTG CTGTGGACTT     540
TCTCGCTGTG ATTTCTTCCT AACAGAGGAT GGGAAAGTTT ATTTGAATGA ACTC           594
```

(2) INFORMATION FOR SEQ ID NO:19:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
                 (A) ORGANISM: Streptococcus oralis (xi) SEQUENCE DESCRIPTION: SEQ ID NO:19:

```
TTTCTTGAAG TTTTGAAAAT GCCTTATGTC GGCTGCAATA TCCTGTCATC AAGTCTTGCC      60

ATGGATAAAA TTACGACCAA GCGTGTTTTA GAATCTGTAG GGATTGCCCA AGTACCTTAT     120

GTGGCTATCG TCGAAGGTGA TGATGTGACT GCTAAAATAG CTGAAGTTGA AGAAAAATTG     180

ACTTATCCAG TCTTCACGAA GCCGTCAAAC ATGGGTTCAA GTGTCGGTAT TTCTAAGTCT     240

GAAAACCAAG AGGAACTCCG TCAAGCTTTG GAACTTGCCT TCCAATATGA CAGCCGTGTC     300

TTGGTAGAGC AAGGGGTGAA TGCCCGTGAA ATCGAGGTTG GTCTCTTGGG CAACTACGAT     360

GTGAAGAGCA CGCTTCCTGG TGAAGTGGTC AAGGATGTTG CCTTTTATGA CTATGATGCC     420

AAGTATATTG ACAACAAGAT TACCATGGAC ATCCCAGCCA AGATTAGTGA TGATGTAGTA     480

GCTGTCATGC GTCATAATGC AGAAACTGCC TTCCGTGCGA TCGGTGGCCT CGGTCTGTCT     540

CGTTGTGATT TCTTCTATAC AGATAAGGGC GAGATTTTCC TAAACGAGCT T             591
```

(2) INFORMATION FOR SEQ ID NO:20:

(i) SEQUENCE CHARACTERISTICS:
                 (A) LENGTH: 591 base pairs
                 (B) TYPE: nucleic acid
                 (C) STRANDEDNESS: single
                 (D) TOPOLOGY: linear (ii) MOLECULE TYPE: DNA (genomic)

(vi) ORIGINAL SOURCE:
                 (A) ORGANISM: Streptococcus salivarius (xi) SEQUENCE DESCRIPTION: SEQ ID NO:20:

```
TTCCTCGAAA CCCTCAAATT GCCATATGTG GGTACTAATG TTCTTTCTTC AAGTGTGGCT      60

ATGGACAAGA TTATGACCAA GCATATTCTT GAAGTTGCTG GTGTGCCTCA GGTTGCCTAT     120

ACAGTCTTCA TCGAGGGTGA AGATTTGGAA GCAGCAGTAG CAGAGACGCT TGAAAAATTG     180

ACCTTCCCAG TGTTTGTCAA ACCTGCTAAT ATGGGGTCAT CTGTTGGGAT TTCTAAAGCT     240

GAAAATGAAG CAGAGCTTCG TGCAGCGATT GATCTGGCTC TCAAATATGA TAGCCGTATC     300

TTGATTGAGC AAGGTGTGGT TGCCCGTGAA ATCGAGGTTG GTATCCTTGG CAATACGACT     360

GTCAAAACGA CTAATCCAGG TGAAGTAGTC AAAGATGTGG CTTTCTATGA CTATCAAGCC     420

AAGTACATTG ACAATAAGAT TACCATGGAC ATCCCAGCTC ACGTGCCTGC AGAAGTCATG     480

ACGCAAATGC GTGTCTATGC GGCCAAGGCC TTCCGTGCCC TCGGTGGTTG TGGTCTTGCC     540

CGCTGTGATT TCTTCCTGAC AGAGGATGGA GCCATCTACC TTAACGAGCT C             591
```

(2) INFORMATION FOR SEQ ID NO:21:

(i) SEQUENCE CHARACTERISTICS:
                 (A) LENGTH: 591 base pairs
                 (B) TYPE: nucleic acid
                 (C) STRANDEDNESS: single
                 (D) TOPOLOGY: linear (ii) MOLECULE TYPE: DNA (genomic)

(vi) ORIGINAL SOURCE:
                 (A) ORGANISM: Streptococcus gordonii (xi) SEQUENCE DESCRIPTION: SEQ ID NO:21:

-continued

```
TTCCTAGAAG TCCTCAAAAT GCCTTATGTC GGCTGTAATA TTCTATCTTC TAGCCTGGCC     60

ATGGATAAAA TTACGACCAA GCGAGTTCTG GAATCAGCAG GTATTGCTCA AGTACCTTAT    120

GTAGCGGTGG TTGATGGTGA GGATCTAGAG CAAAAAATCC AGGAAATTGA AGAGAAACTG    180

TCCTATCCCG TCTTCACCAA ACCTTCTAAT ATGGGCTCCA GTGTCGGCAT TCAAAATCT     240

GATAATCAGG AAGAACTGCG TGCTTCTCTG GACCTGGCTT TCAAATACGA TAGTCGGGTA    300

CTAGTCGAGC AAGGTGTAAC AGCTCGTGAG ATTGAGGTTG GACTTCTTGG TAACACTGAT    360

GTCAAAAGCA GTCTTCCAGG GGAAGTTGTT AAGGATGTGG CTTTCTATGA TTATCAAGCC    420

AAATATATTG ACAATAAAAT CACCATGGCA ATCCCAGCTC AGCTTCCTGA AGGTGTTGTG    480

AATACTATGC GTCAAAATGC CGAGACAGCT TTTCGTGCTA TTGGTGGGTT AGGACTATCT    540

CGCTGTGATT TTTTCTACAC AGAAGATGGT CAGGTCTTTC TTAATGAGCT C             591

(2) INFORMATION FOR SEQ ID NO:22:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Streptococcus sanguis (xi) SEQUENCE DESCRIPTION: SEQ ID NO:22:

TTCCTAGAAG TGCTCAAAAT GCCTTATGTC GGCTGTAATA TTTTATCTTC TAGCTTAGCC     60

ATGGATAAAA TCACGACCAA GCGAGTGCTG GAATCAGCAG GAATAGCCCA AGTGCCTTAT    120

GTGGCGCTGG TCGATGGCGA GGATCTAGAG CAAAAAATCC AAGAAATCGA GGAGAAATTG    180

ACCTATCCAG TCTTCACCAA ACCTTCTAAT ATGGGCTCCA GTGTCGGCAT TTCTAAATCG    240

GAGACCAAGC AGAACTGCGT GCTTCTCTGG ACCTGGCTTT CAATACGACG CCGAGTACTG    300

GTTGAGCAAG GAGATCGAAC GGCTCGCGAG ATTGAGGTTG GGCTTTTGGG CAATGTTGAC    360

GTCAAGAGTA CCCTACCTGG AGAAGTGGTC AAGGACGTGG CTTTTTATGA CTACGAAGCC    420

AAATACATTG ATAATAAAAT TACCATGGAT ATTCCGGCCA AGATTCCAGA AGAAGTGGTG    480

AGTCTGATGC GTCAAAATGC AGAGGCAGCT TTCCGAGCTC TGGGCGGTCT GGGGCTGTCC    540

CGTTGTGATT TCTTCTATGC AGAAGATGGT CAGGTCTTCC TTAATGAGCT C             591

(2) INFORMATION FOR SEQ ID NO:23:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Streptococcus anginosus (xi) SEQUENCE DESCRIPTION: SEQ ID NO:23:

TTTCTTGAAG TGTTGAAAAT GCCTTATGTG GGTTGCAATA TCCTTTCTTC TAGTGTTGCT     60

ATGGACAAAA TCACGACAAA ACGAGTGTTA GCTTCTGCTG GCATTCCGCA AGTTCCCTAT    120

GTAGCAGTGA TTGAAGGGGA AAATATAGAC GAAAAGATTG CAGCAGTAGA AGCCAATCTG    180

ACTTATCCAG TTTTTACAAA ACCGTCAAAT ATGGGATCTA GTGTCGGCAT TTCTAAGTCT    240
```

```
GAAAATCAAG ATGAATTGCG CTCTGCTCTT GAATTGGCTT TCAAATATGA TAGCCGTGTC      300

TTGATTGAGC AAGGTGTCAA TGCGCGTGAA ATTGAAGTTG GTTTACTTGG AAATGAAGGA      360

GCCAAAAGCA GTTTGCCAGG TGAGGTAGTG AAAGATGTTG CTTTCTATGA CTACGAAGCC      420

AAGTACATTG ACAACAAAAT CACCATAGAT ATTCCTGCAA AACTCTCTGA AGATGTCATT      480

GCCACTATGC GGCAATATGC TGAAAAACGA TTCCATGCTA TTGGCGGTGT TGGTTTAGCT      540

CGCTGCGATT TCTTTTATAC TGATAAGGGC GAGATTTTCC TTAATGAGTT A              591

(2) INFORMATION FOR SEQ ID NO:24:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus constellatus (xi) SEQUENCE DESCRIPTION: SEQ ID NO:24:

TTTCTTGAAG TGTTGAAAAT GCCTTATGTG GGTTGTAATA TCCTTTCTTC TAGTGTTGCC       60

ATGGACAAAA TCACAACAAA ACGAGTGTTA GCTTCTGCTG GCATTCCGCA AGTTCCCTAT      120

GTAGCAGTGA TTGAAGGGGA AAATATAGAC GAAAAGATTG CAGAAGTAGA GGCAAATCTA      180

ACTTATCCAG TTTTTACAAA ACCGTCAAAT ATGGGCTCTA GTGTCGGCAT TTCTAAGTCT      240

GAAAATCAAG ATGAATTGCG TTCTGCTCTT GAATTGGCTT TCAAATATGA TAGCCGTGTC      300

TTGATTGAGC AAGGTGTCAA TGCGCGTGAA ATTGAAGTTG GTTTACTTGG AAATGAAGGA      360

GCCAAAAGCA GTTGGCCAGG TGAGGTAGTG AAAGATGTTG CTTTCTATGA CTACGAAGCC      420

AAGTACATTG ACAACAAAAT CACCATGGAT ATTCCTGCAA AACTCTCTGA AGATGTCATT      480

GTCACTATGC GGCAATATGC AGAAAAAGCT TTCCATGCTA TTGGCGGTGT TGGTTTAGCT      540

CGCTGCGATT TCTTTTATAC TGATAAGGGC GAGATTTTCC TTAATGAGTT A              591

(2) INFORMATION FOR SEQ ID NO:25:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus intermedius (xi) SEQUENCE DESCRIPTION: SEQ ID NO:25:

TTTCTTGAAG TGTTGAAAAT GCCTTATGTT GGCTGCAATA TTCTTTCGTC GAGTATTGCG       60

ATGGATAAAA TCACAACTAA ACGTGTGTTA GCTTCTGCTG GTATTCCTCA AGTACCGTAT      120

GTAGCCGTAG TGGAAGGGGA AGATGTAGAA GAAAAGATTG CAGAAGTAGA AGTTAATCTG      180

ACTTATCCAG TCTTTACTAA ACCATCAAAT ATGGGTTCTA GTGTTGGCAT TTCTAAATCT      240

GAAAACAAAG ATGAATTGTG TTCTGCTCTT AAGTTAGCTT TTAAATACGA TACCCGTGTC      300

TTGATTGAGC AAGGTGTCAA TGCGCGTGAA ATTGAAGTTG GTTTATTTGG GAACGAAGGA      360

GCTAAAAGTA GTTTACCAGG TGAAGTGGTG AAAGATGTCG CTTTTTATGA TTACGAAGCC      420
```

```
AAGTACATTG ACAATAAAAT TACTATGGAT ATCCCTGCAA AACTCTCTGA AGATGTTATT      480

GCCACTATGT GTGACTATGC TGAAAAAGCT TTCCATGCAA TTGGTGGCGT TGGGTTATCT      540

CGTTGTGATT TCTTTTATAC TAATAAGGGT GAGATTTTCC TCAATGAGTT A              591

(2) INFORMATION FOR SEQ ID NO:26:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus avium (xi) SEQUENCE DESCRIPTION: SEQ ID NO:26:

TTCTTAGAGA CATTGGATAT GCCTTACGTT GGTGCGGGTG TAATGACGAG TGCTTGTGCA       60

ATGGACAAAA TTATGACGAA ATACATTTTG CAGGCAGCTG GCATCCCGCA GGTTCCTTAC      120

GTTCCAGTCC TAAAAAACCA ATGGAAAGAA AATCCTAAAC AAATTTTTGA TAAATGTGAG      180

GGAACGTTAC TGTATCCAAT GTTTGTCAAA CCGGCGAATA TGGGCTCTAG CGTAGGAATT      240

TCACGTGCTG AAAATCGCGA AGAACTGCAA AACGCATTGC AAGAAGCTTA TCGCTATGAT      300

TCAAGAGCTT TAGTTGAGCA AGGCATCGAT GCTTGTGAGA TTGAAGTTGC GGTTTTAGGC      360

AATGACGATG TGCGGACGAC ATTACCTGGT GAGGTCGTAA AGGAAGAAGC ATTCTATGAT      420

TACAATGCTA AATACATCAA TAATACGATT CAAATGGCAA TTCCAGCGGA TGTGCCGGAA      480

GATGTGATGC AAAAAGCTCG CGATTTTGCA AAATCAGCCA TATCAATGTT AGGTGGATCA      540

GGATTAAGTC GCTGCGACTT TTTCTTGACA AATAAAAATG AATTATTCTT GGATGAGCTG      600

(2) INFORMATION FOR SEQ ID NO:27:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus pseudoavium (xi) SEQUENCE DESCRIPTION: SEQ ID NO:27:

TTTTTAGAAA CATTAGATAT GCCTTACGTA GGGGCTGGCG TGATGACTAG TGCTTGTGCG       60

ATGGACAAGA TTATGACGAA GTATATCTTG CAGGCAGCTG GGATTCCACA AGTACCTTAT      120

GTACCGGTGT TAAAGAATCA ATGGAAAGAA ACCCTAAAC AAGTTTTTGA TAAATGTGAA       180

GGAACCTTGT TGTATCCAAT GTTTATCAAA CCAGCGAATA TGGGTTCTAG CGTCGGAATT      240

AGCCGCGCTG AGAATCGCGA AGAACTACAA AATGCCTTGA AAGAAGCCTA TCGGTATGAT      300

TCGCGGGCAT TAGTTGAACA AGGAATCGAT GCTCGTGAAA TTGAGGTTGC CGTTTTAGGC      360

AACGATGACG TTCGAACAAC GTTGCCTGGC GAAGTCGTGA AGGAAGTAGC CTTCTATGAT      420

TACAATGCTA AGTACATCGA TAATACGATT CAAATGGCGA TTCCAGCAGA AGTGCCGAAA      480

GAAGTGATGC AAAAAGCTCG GGAGTATGCA AAATTAGCTT ACACGATGTT AGGCGGATCG      540

GGCTTGAGCC GTTGCGACTT CTTTTTGACC AATAAAAATG AATTATTCTT AAATGAGTTA      600
```

```
(2) INFORMATION FOR SEQ ID NO:28:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Enterococcus cecorum (xi) SEQUENCE DESCRIPTION: SEQ ID NO:28:

TTTTTAGAAA CTTTGAAGAT GCCTTATGTC GGTACAGGGG TTTTAGCAAG TGCGTGTGGC      60

ATGGATAAAA TTATGACCAA ATATGTCTTA CAAGCAGGTG GCATCCCACA AGTGCCTTAT     120

GTTCCGGTAT TAGCCATGCA TTGGAAACAA GATCCACAAT TAATCTTTGA ACATTGCGAA     180

GGTTCCTTAT TATACCCAAT GTTTGTCAAA CCGGCGAATA TGGGTTCAAG CGTGGGAATT     240

TCTAAGGCTG AAAACCGTGA TGAATTAGAA GCAGCTTTAA ATGAAGCATT CTTATATGAT     300

ACACGCGGGA TTATCGAGCA AGGAATTGAA GTTGCTGTTT TAGAAATGAA GAATGTTCGT     360

ACGACTATGG CGGGTGAAAT TGTTAAAGAT GTCGCTTTTT ACGATTATAA TTCAAAATAT     420

ATCGACAACA AAATTGTGAT GCAAATCCCG GCACAAGTAC CTGATGAAGT GCAACAAAAA     480

GCACAAGAAT ATGCCAAAAA AGCTTATACC ATGCTTGGTG GCTCAGGATT AAGTCGTTGT     540

GATTTCTTCT TAACCAATAA GAACGAATTA TTCTTAAATG AATTA                    585

(2) INFORMATION FOR SEQ ID NO:29:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Enterococcus saccharolyticus (xi) SEQUENCE DESCRIPTION: SEQ ID NO:29:

TTCCTTGAAA CCATTCGTAT GCCGTATGTG GGTGCCGGTG TCTTAACAAG TGCCTGTGGA      60

ATGGATAAGA TTATGACAAA ATATATCTTA CATTCAGCTG GAATTCCACA AGTTCCTTAT     120

GTACCCGTGT TGAAAAATCA ATGGAAAGAA AATCCAAAAC AAATTTTTGA ACAATGTGAA     180

GGCTCTCTAC GTTACCCAAT GTTTGTTAAG CCAGCGAATA TGGGATCAAG TGTAGGCATT     240

TCAAAAGCCG AAAATCGCGT CGAGCTGCAA AATGCATTAG AAGAAGCTTA CAAGTATGAT     300

AACCGTGCAG TGATTGAGCA GGGCATTGAA GCACGTGAAA TCGAAGTAGC GATTTTAGGG     360

AATGAAGATG TTCGTACAAC GATGGCGGGC GAAATTGTTA AAGATGTGGC GTTTTATGAT     420

TATAATTCAA AATATATCGA TAACAGTATT GTGATGCAAA TTCCAGCACA AGTTCCTGAT     480

GAAGTGCAAG AAAAAGCACA AGAATATGCC AAACTTGCTT ATACGATGTT AGGTGGAAGT     540

GGATTAAGCC GTTGTGATTT CTTTTTAACA AATAAAAATG AATTATTCTT AAATGAATTA     600

(2) INFORMATION FOR SEQ ID NO:30:

(i) SEQUENCE CHARACTERISTICS:
        (A) LENGTH: 600 base pairs
        (B) TYPE: nucleic acid
        (C) STRANDEDNESS: single
        (D) TOPOLOGY: linear
```

(ii) MOLECULE TYPE: DNA (genomic)

(vi) ORIGINAL SOURCE:
    (A) ORGANISM: Enterococcus dispar (xi) SEQUENCE DESCRIPTION: SEQ ID NO:30:

| | | | | | |
|---|---|---|---|---|---|
| TTCTTAGAAA | CCATTGATAT | GCCTTATATT | GGGGCGGGAG | TTTTAACAAG | TGCTTGTGGC | 60
| ATGGATAAAA | TCATGACCAA | ATATATTCTA | CAAGCTGCGG | GTATTCCACA | AGTACCTTAT | 120
| GTGCCAGTCT | TGAAAAATCT | GTGGAAAGAA | ATCCTAAAC | AAATTTTTGA | GCAATGTGAA | 180
| GGAACTCTGT | TATACCCAAT | GTTTGTTAAG | CCAGCCAACA | TGGGTTCTTC | TGTCGGCATT | 240
| TCAAAAGCTG | AAAACAGAGA | AGAATTGCAA | AATGCATTGC | AAGAAGCGTA | TAAATATGAC | 300
| ACGCGGGCAA | TTGTCGAACA | AGGAATTGAA | CGCGGGGAAA | TTGAAGTTGC | AATTTTAGGT | 360
| AACGAAGATG | TTCGGACTAC | TTTACCTGGT | GAAATTGTAA | AAGATGTCGC | TTTTTATGAC | 420
| TATAATTCCA | AATATATCGA | CAACCAAATT | ATCATGCAGA | TTCCGGCTGA | AATACCAGAA | 480
| GACGTACAAC | AAAAAGCACA | AGATTTTGCT | AAAAAAGCCT | ACGTTATGCT | AGGTGGAAGT | 540
| GGCTTGTCGC | GTTGTGATTT | CTTTTTAACG | AATAAAAATG | AATTGTTCTT | AAATGAATTA | 600

(2) INFORMATION FOR SEQ ID NO:31:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus hirae (xi) SEQUENCE DESCRIPTION: SEQ ID NO:31:

| | | | | | |
|---|---|---|---|---|---|
| GGGAGCACAA | TCTTTTGAAG | ATTACTTTAC | TATATGGTGG | ACGCAGTGCA | GAACATGATG | 60
| TTTCAGTTCT | TTCAGCGTTT | TCAGTCTTAA | ATGCTATTTA | TTATACGTAC | TATCAAGTTC | 120
| AACTGATATT | TATCAGCAAA | GAAGGTCAAT | GGGTGAAAGG | CCCTTTGTTA | ACAGAGAAAC | 180
| CAACGAGCAA | AGAAGACTTA | CATTTGACAT | GGGACCCAAG | CGGAAAAGTG | ACAGATGGCT | 240
| TTACGGGAAG | AGTGATCAAT | CCTGGAGAAA | TCAAAGAAGA | AGGAACGATT | GTTTTCCCTG | 300
| TCTTACACGG | ACCTAATGGT | GAAGATGGAA | CGATTCAAGG | ATTTTTGGAA | ACATTGAACT | 360
| TGCCATATGT | CGGCGCTGGC | GTTTTAACAA | GTGCTTGTGC | AATGGATAAG | ATCATGACCA | 420
| AATACATTTT | GCAAGCGGCA | GGGGTGCCAC | AAGTTCCTTA | TGTCCCTGTT | TTGAAAAATC | 480
| AATGGAAAGA | AAATCCTAAA | AAAATCTTTG | ATCAATGTGA | AGGGTCTTTG | CTTTACCCAA | 540
| TGTTTGTCAA | ACCAGCAAAT | ATGGGTTCAA | GTGTAGGGAT | CTCTAAAGCG | GAGAACCGTG | 600
| AAGAACTGCA | AAATGCGCTT | GCATTAGCTT | ATCAATATGA | TTCTCGTGCG | ATCGTTGAGC | 660
| AAGGGATCGA | AGCACGTGAA | ATTGAAGTAG | CTGTTTTAGG | GAATGAAGAC | GTGCGTACCA | 720
| CATTACCTGG | TGAAGTAGTC | AAAGATGTTG | CATTCTATGA | TTATGATGCG | AAATACATCA | 780
| ACAATAAGAT | TGAAATGCAA | ATCCCAGCTG | AAGTACCGGA | AGAGGTCTAT | CAAAAAGCGC | 840
| AGGAATATGC | AAAAATTGCG | TATACAATGC | TAGGTGGGAG | TGGCTTGAGC | CGTTGTGATT | 900
| TCTTCTTGAC | GAATAAAAAT | GAACTATTCC | TAAATGAGTT | AAATACAATG | CCTGGATTCA | 960
| CGCAATTTAG | CATGTATCCA | TTATTGTGGG | AAAACATGGG | CTTGAAGTAT | GGCGATTTGA | 1020
| TCGAAGAATT | GATTCAATTA | GGAATCAATC | GTTTTAATCA | ACGACAAGGT | TTTTTTAACG | 1080

CAAACGAATA GACAA                                                        1095

(2) INFORMATION FOR SEQ ID NO:32:

(i) SEQUENCE CHARACTERISTICS:
        (A) LENGTH: 1001 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus gallinarum (xi) SEQUENCE DESCRIPTION: SEQ ID NO:32:

AAATGTGGAA GAATTAGTTT TGGTAGAAAC AATGAATACA GGAGGAATTT CTTTTGAAAA          60

TTATTTTATT ATATGGCGGA CGCAGTGCAG AGCATGATGT ATCGCTTCTA TCCGCTTTTT         120

CAGTAGTCAA TGCTGTATAT TATAATTACT ACCAAGTACA ATTAGTAATG ATCACGAGAG         180

ATGGCCAGTG GCTAAAAGGC TCTTTATTGA CTGAAGCCCC TACATCCAAA GAAGTGTTGA         240

ATCTGACGGA TTCGGCTTAC CAAGGGACGC CGATCCAACC TGGTGAGATC AAGGAAGAGG         300

ATGCGATTGT TTTTCCGCTG CTCCACGGAC CAAATGGAGA AGATGGAACG ATCCAAGGTT         360

TTCTAGAGAC CATCGGCATG CCTTATGTAG GCGCAGGGGT TTTAACTAGT GCCTGTGGCA         420

TGGATAAGAT TATGACCAAA TATATCTTGC AGGCGGCGGG GATTCCGCAA GTTCCTTATG         480

TACCCGTTCT TAAAAACTAT TGGAAAGAAA ATCCTAAAAA AGTATTTGAA CAATGTGAAG         540

GCAGTCTTTT GTATCCAATG TTTATCAAAC CTGCCAATAT GGGTTCAAGT GTTGGGATCA         600

CAAAAGCTGA AAATCGGGAA GAATTGCAAA ATGCACTTCA AGAAGCCTAC CGTTATGATA         660

CACGAGCGAT CGTAGAACAA GGGATCGAAG CTCGCGAAAT CGAAGTCGCT GTTCTTGGAA         720

ATGAAGATGT GCGTACAACA ATGCCCGGCG AGATCGTTAA AGATGTAGCT TTTTATGATT         780

ACAATTCGAA GTATCTTGAC AATAAGATTG AGATGCAGAT CCCAGCTCAA ATTCCTGAGG         840

AGACACAAGC GAAAGCGCAA GAGTTTGCCA AAAAAGCTTA TACGATGCTT GGAGGAAGCG         900

GCCTCAGCCG CTGCGACTTT TTCTTGACGA ACAAAAACGA ATTATTCCTG AATGAATTGA         960

ACACCATCCC CGCTTTACAA GCCGAATTCT GCAGATATCC A                           1001

(2) INFORMATION FOR SEQ ID NO:33:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus faecium (xi) SEQUENCE DESCRIPTION: SEQ ID NO:33:

TTCTTAGAGA CATTGAATAT GCCTTATGTC GGCGCAGGCG TATTGACCAG TGCATGTGCC          60

ATGGATAAAA TCATGACCAA GTATATTTTA CAAGCTGCTG GTGTGCCGCA AGTTCCTTAT         120

GTACCAGTAC TTAAGAATCA ATGGAAAGAA AATCCTAAAA AAGTATTTGA TCAATGTGAA         180

GGTTCTTTGC TTTATCCGAT GTTTGTCAAA CCTGCGAATA TGGGTTCTAG TGTCGGCATT         240

ACAAAGGCAG AAAACCGAGA AGAGCTGCAA AATGCTTTAG CAACAGCCTA TCAGTATGAT         300

-continued

```
TCTCGAGCAA TCGTTGAACA AGGAATTGAA GCGCGCGAAA TCGAAGTTGC TGTATTAGGA      360

AATGAAGATG TTCGGACGAC TTTGCCTGGC GAAGTCGTAA AAGACGTAGC ATTCTATGAT      420

TATGAAGCCA AATATATCAA TAATAAAATC GAAATGCAGA TTCCAGCCGA AGTGCCGGAA      480

GAAGTTTATC AAAAAGCGCA AGAGTACGCG AAGTTAGCTT ACACGATGTT AGGTGGAAGC      540

GGATTGAGCC GGTGCGATTT CTTTTTGACA AATAAAAATG AATTATTCCT GAATGAATTA      600
```

(2) INFORMATION FOR SEQ ID NO:34:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO:34:

GCATCGAATG CATGTCTCGG GT      22

(2) INFORMATION FOR SEQ ID NO:35:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO:35:

GGNGARGAYG GNWSNHTNCA RGGN      24

(2) INFORMATION FOR SEQ ID NO:36:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "N is i (inosine)."

(xi) SEQUENCE DESCRIPTION: SEQ ID NO:36:

GTRAANCCNG GNADNGTRTT      20

POLYNUCLEOTIDES AND THEIR USE FOR DETECTING ENTEROCOCCI AND STREPTOCOCCI BACTERIAL STRAINS

BACKGROUND OF THE INVENTION

The present invention pertains to polynucleotides derived from previously unknown sequences internal to the ddl gene coding for D-Alanine:D-Alanine ligase of various bacterial strains belonging to the Enterococci or to the Streptococci genus. This invention also relates to the use of the polynucleotides as oligonucleotide primers or probes for detecting and identifying specifically Enterococci or Streptococci in a biological sample.

In another embodiment, the present invention is directed to the full length coding sequences of the ddl genes from Streptococci and Enterococci and to the polypeptides expressed by these full length coding sequences.

Further, this invention relates to the use of the expressed polypeptides to produce specific monoclonal or polyclonal antibodies that serve as detection means in order to characterize a specific species or group of species of Streptococci or Enterococci.

The present invention is also directed to diagnostic methods for detecting specifically strains of Enterococci or streptococci expected to be contained in a biological sample. The diagnostic methods use the oligonucleotide probes or primers as well as the antibodies of the invention.

Glycopeptide antibiotics, such as vancomycin and teicoplanin, inhibit peptidoglycan synthesis in Enterococci and are used to treat severe infections caused by Gram-positive bacteria. Glycopeptides do not interact directly with cell wall biosynthetic enzymes, but form complexes with peptidoglycan precursors and prevent their incorporation into the cell wall. Consequently, the activity of glycopeptides is determined by the substrate specificity of the enzymes that affect the structure of peptidoglycan precursors.

Acquisition of glycopeptide resistance results from the transfer of mobile genetic elements that encode enzymes for the synthesis of low-affinity precursors and elimination of the high-affinity precursors normally produced by the host. Among the enzymes of altered substrate specificity found in glycopeptide resistant Enterococci strains, D-Ala:D-Ala ligase is a main component. More precisely, usually, the D-Ala:D-Ala related enzymes synthesize D-alanyl-D-Alanine. In vancomycin-resistant Gram-positive bacteria, structurally related enzymes synthesize D-Alanyl:D-Lactate or D-Alanyl:D-Serine.

PCT Application No. PCT/FR91/00855 (Courvalin et al.), published on May 14, 1992, discloses a nucleotide sequence from the *Enterococcus faecium* strain BM4147, the Van A gene, that encodes a D-Ala:D-Lac ligase of wide specificity. D-Ala:D-Lac ligase is involved in the resistance of this bacterial strain to the glycopeptide antibiotics vancomycin and teicoplanin. This PCT Application discloses a pair of degenerate primers, V1 and V2, that can be used as primers or probes in order to detect, under non-stringent hybridization conditions, Enterococcus strains that exhibit resistance to glycopeptide antibiotics. Nevertheless, there continues to exist a need in the art for polynucleotides specific for bacterial strains of the Streptococci and Enterococcus genuses.

SUMMARY OF THE INVENTION

Accordingly, this invention aids in fulfilling this need in the art. In particular, this invention provides a purified polynucleotide that hybridizes specifically under stringent conditions with a nucleic acid encoding a D-alanine:D-alanine ligase of a given species or a given group of species belonging to the Streptococci genus or to the Enterococci genus, wherein said purified polynucleotide:

a) has from 12 to 1095 nucleotides;

b) is internal to a polynucleotide of the streptococci ddl gene amplified by the following degenerate pair of primers, said polynucleotide being from about 600 to about 1100 bp in length:

```
                                       SEQ ID NO:35
V1: 5'-GGX GAA GAT GGX TCX TTX CAA GGX-3'
           G   C       AG  C       G
                           A

SEQ ID NO:36
V2: 3'-TTA TGI TAI GGI CCI AAA TG-5'
           G   A           G        ;
               G
``` wherein X represents any DNA nucleotide (A, T, G, or C) and I represents Inosine; and c) does not hybridize with the genome of a Streptococcus strain or of an Enterococcus strain belonging to another species or another group of species under stringent hybridization conditions.

This invention also provides a purified polynucleotide that hybridizes specifically under stringent conditions with a nucleic acid encoding a D-alanine:D-alanine ligase of a given species belonging to the Streptococci genus. The purified polynucleotide comprises a nucleic acid sequence selected from the group consisting of:

a) 5'-GTCGAAGGTGATGATATGAC-3' (SEQ ID N°1)

b) 3'-GACAGTACGCAGTCTTACGTC-5' (SEQ ID N°2)

c) 5'-ATTGAAGGCGAGCCTTTAGAAAG-3' (SEQ ID N°3)

d) 3'-CTAGGACAATAGCAAC-5' (SEQ ID N°4)

e) 5'-TGCAGAAGTAGAGGCAAATC-3' (SEQ ID N°5)

f) 3'-TTCCTCGGTTTTCGTCAACCG-5' (SEQ ID N°6)

g) 5'-GCAGCAGTAGCAGAGACGCT-3' (SEQ ID N°7)

h) 3'-CACGGACGTCTTCAGTACTG-5' (SEQ ID N°8)

i) 5'-GTCGATGGCGAGGATCTAGAGC-3' (SEQ ID N°9)

j) 3'-TGCCGAGCGCTCTAACTCCA-5' (SEQ ID N°10)

k) 5'-TGAAATCGAGGTTGGCCTAC-3' (SEQ ID N°11)

l) 3'-TTCCC(G/T)CTCTAAAAGGATTTGC-5' (SEQ ID N°12)

m) 5'-CTTATGTCGGCTGCAATATCC-3' (SEQ ID N°13)

n) 5'-GTCGATGGCGAGGATCTAGAGC-3' (SEQ ID N°14)

o) 3'-CAGAAGGTCCCCTTCAACAA-5' (SEQ ID N°15)

p) 3'-GACTACGCAGTTTTACGTCTC-5' (SEQ ID N°16)

In another embodiment, this invention provides a pair of purified oligonucleotides capable of amplifying specifically a polynucleotide internal to the ddl gene of a given species belonging to the Streptococci genus. The pair of purified oligonucleotides is selected from the group consisting of:

A) 5'-GTCGAAGGTGATGATATGAC-3' (SEQ ID N°1)
3'-GACAGTACGCAGTCTTACGTC-5' (SEQ ID N°2)

B) 5'-ATTGAAGGCGAGCCTTTAGAAAG-3' (SEQ ID N°3)
3'-CTAGGACAATAGCAAC-5' (SEQ ID N°4)

C) 5'-GCAGCAGTAGCAGAGACGCT-3' (SEQ ID N°7)
3'-CACGGACGTCTTCAGTACTG-5' (SEQ ID N°8)

D) 5'-GTCGATGGCGAGGATCTAGAGC-3' (SEQ ID N°9)
3'-TGCCGAGCGCTCTAACTCCA-5' (SEQ ID N°10)

E) 5'-TGCAGAAGTAGAGGCAAATC-3' (SEQ ID N°5)
3'-TTCCTCGGTTTTCGTCAACCG-5' (SEQ ID N°6)

F) 5'-TGAAATCGAGGTTGGCCTAC-3' (SEQ ID N°11)
3'-TTCCC(G/T)CTCTAAAAGGATTTGC-5' (SEQ ID N°12)

G) 5'-CTTATGTCGGCTGCAATATCC-3' (SEQ ID N°13)
3'-TTCCC(G/T)CTCTAAAGGATTTGC-5' (SEQ ID N°12)

H) 5'-GTCGATGGCGAGGATCTAGAGC-3' (SEQ ID N°14)
3'-CAGAAGGTCCCCTTCAACAA-5' (SEQ ID N°15)

I) 5'-GTCGATGGCGAGGATCTAGAGC-3' (SEQ ID N°14)
3'-GACTACGCAGTTTTACGTCTC-5' (SEQ ID N°16).

In addition, this invention provides a polynucleotide selected from the group consisting of SEQ ID No. 17 to SEQ ID No. 33; a polynucleotide having at least 12 consecutive nucleotides of these SEQ ID numbers; a polynucleotide having at least 12 consecutive nucleotides of a sequence fully complementary to these SEQ ID numbers; and a polynucleotide hybridizing under stringent hybridization conditions with any one of these polynucleotides. A recombinant vector comprising any of these polynucleotides is also provided.

Still further, this invention provides methods for detecting a bacterium belonging to the Streptococci genus or to the Enterococci genus in a biological sample comprising the steps of (a) bringing into contact a purified polynucleotide according to the invention with a biological sample; and (b) detecting hybrid nucleic acid molecule formed between the purified polynucleotide and nucleic acid molecules contained in the biological sample. A kit of the invention for detecting a bacterium belonging to the Streptococci genus or to the Enterococci genus in a biological sample comprises a purified polynucleotide according to the invention, and reagents necessary to perform a nucleic acid hybridization reaction.

Another polynucleotide of the invention comprises the full length coding sequence of a Streptococci or an Enterococci D-Ala:D-Ala ligase containing a polynucleotide sequence. A polypeptide of the invention comprises the expression product of such a polynucleotide. Monoclonal or polyclonal antibody directed against a polypeptide are also contemplated. Another diagnostic kit of the invention for in vitro detection of the presence of a polypeptide in a biological sample comprises a polyclonal or monoclonal antibody of the invention optionally labeled; and a reagent allowing the detection of antigen-antibody complexes formed. The reagent can carry optionally a label or be able to be recognized itself by a labeled reagent. More particularly, the monoclonal or polyclonal antibody need not be labeled itself.

BRIEF DESCRIPTION OF THE DRAWINGS

This invention will be described in greater detail with reference to the drawings in which:

FIG. 1 is a sequence comparison of fragments internal to genes coding for D-Ala:D-Ala ligases from *S. anginosus* (ATCC 33397), *S. constellatus* (ATCC 27823), *S. gordonlii* (ATCC 10558), *S. intermedius* (ATCC 27335), *S. mitis* (NCTC 12261), *S. mutans* (NCTC 10449), *S. oralis* (NCTC 7864), *S. salivarius* (ATCC 9758), and *S. sanguis* (NCTC 7863). Stars indicate identical nucleotides in all sequences. Dots indicate gaps introduced to optimize alignments.

DETAILED DESCRIPTION

Figure 2:
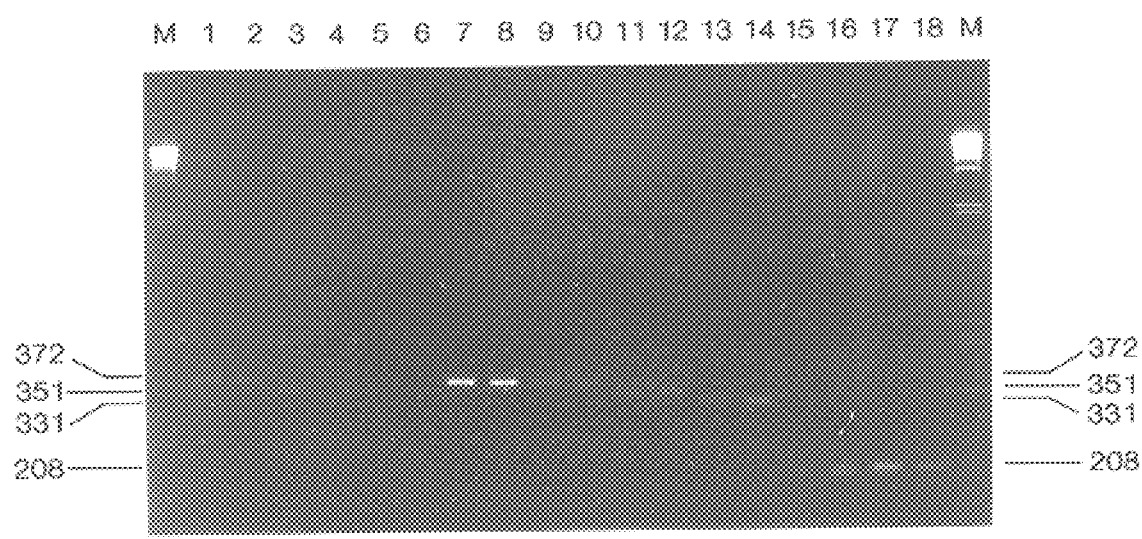
FIG. 2. First step PCR analysis of total DNA from reference and wild strains of viridans streptococci. Lanes:1, *S. mitis* NCTC 12261; 2, *S. oralis* NCTC 7864; 3, *S. mutans* NCTC 10449; 4, *S. salivarius* ATCC 9758; 5, *S. gordonii* ATCC 10558; 6, *S. sanguis* NCTC 7863; 7 and 8, *S. mitis*; 9 and 10, *S. oralis*; 11 and 12, *S. mutans*; 13 and 14, *S. salivarius*; 15 and 16, *S. gordonii*; 17 and 18, *S. sanguis*. M, bacteriophage λ DNA (Pharmacia) digested with PsiI used as a size standard. PCR products were resolved by electrophoresis on a 2% agarose-Tris-borate-EDTA gel containing 0.5 µg of ethidium bromide per ml. The sizes of the PCR products are indicated in base pairs.

It has now been discovered that bacteria from the Streptococci genus also carry a ddl gene counterpart, a portion of which can be amplified using the degenerate pair of primers V1 and V2 previously described. This is a surprising result that could not have been deduced from the prior art, since ddl genes have never been described for bacteria belonging to the Streptococci genus.

Thus, novel polynucleotides corresponding to an internal portion of the ddl gene encoding D-Ala:D-Ala ligases from various strains of Streptococci have been isolated and sequenced, and it has been surprisingly demonstrated that these new polynucleotides make it possible to design oligonucleotide probes or primers that are specific for particular species or groups of species belonging to the Streptococci genus. These polynucleotides include the following:

a) 5'-GTCGAAGGTGATGATATGAC-3' (SEQ ID N°1)
b) 3'-GACAGTACGCAGTCTTACGTC-5' (SEQ ID N°2)
c) 5'-ATTGAAGGCGAGCCTTTAGAAAG-3' (SEQ ID N°3)
d) 3'-CTAGGACAATAGCAAC-5' (SEQ ID N°4)
e) 5'-TGCAGAAGTAGAGGCAAATC-3' (SEQ ID N°5)
f) 3'-TTCCTCGGTTTTCGTCAACCG-5' (SEQ ID N°6)
g) 5'-GCAGCAGTAGCAGAGACGCT-3' (SEQ ID N°7)
h) 3'-CACGGACGTCTTCAGTACTG-5' (SEQ ID N°8)
i) 5'-GTCGATGGCGAGGATCTAGAGC-3' (SEQ ID N°9)

j) 3'-TGCCGAGCGCTCTAACTCCA-5' (SEQ ID N°10)
k) 5'-TGAAATCGAGGTTGGCCTAC-3' (SEQ ID N°11)
l) 3'-TTCCC(G/T)CTCTAAAAGGATTTGC-5' (SEQ ID N°12)
m) 5'-CTTATGTCGGCTGCAATATCC-3' (SEQ ID N°13)
n) 5'-GTCGATGGCGAGGATCTAGAGC-3' (SEQ ID N°14)
o) 3'-CAGAAGGTCCCCTTCAACAA-5' (SEQ ID N°15)
p) 3'-GACTACGCAGTTTTACGTCTC-5' (SEQ ID N°16).

In addition, novel polynucleotides corresponding to an internal portion of the ddl gene encoding D-Ala:D-Ala ligases from various strains of Enterococci have been isolated and sequenced. These novel polynucleotides are useful for the design of oligonucleotide probes or primers that are specific for particular species or groups of species belonging to the Enterococci genus. These purified polynucleotides are also part of the present invention and include the following:

```
SEQ ID NO: 26
Enterococcus avium D-alanine:
D-alanine ligase gene, partial cds.
    1 TTCTTAGAGA CATTGGATAT GCCTTACGTT GGTGCGGGTG TAATGACGAG

51 TGCTTGTGCA ATGGACAAAA TTATGACGAA ATACATTTTG CAGGCAGCTG

101 GCATCCCGCA GGTTCCTTAC GTTCCAGTCC TAAAAAACCA ATGGAAAGAA

151 AATCCTAAAC AAATTTTTGA TAAATGTGAG GGAACGTTAC TGTATCCAAT

201 GTTTGTCAAA CCGGCGAATA TGGGCTCTAG CGTAGGAATT TCACGTGCTG

251 AAAATCGCGA AGAACTGCAA AACGCATTGC AAGAAGCTTA TCGCTATGAT

301 TCAAGAGCTT TAGTTGAGCA AGGCATCGAT GCTTGTGAGA TTGAAGTTGC

351 GGTTTTAGGC AATGACGATG TGCGGACGAC ATTACCTGGT GAGGTCGTAA

401 AGGAAGAAGC ATTCTATGAT TACAATGCTA AATACATCAA TAATACGATT

451 CAAATGGCAA TTCCAGCGGA TGTGCCGGAA GATGTGATGC AAAAAGCTCG

501 CGATTTTGCA AAATCAGCCA TATCAATGTT AGGTGGATCA GGATTAAGTC

551 GCTGCGACTT TTTCTTGACA AATAAAAATG AATTATTCTT GGATGAGCTG

SEQ ID NO: 27
Enterococcus pseudoavium D-alanine:
D-alanine ligase gene, partial cds.
    1 TTTTTAGAAA CATTAGATAT GCCTTACGTA GGGGCTGGCG TGATGACTAG

51 TGCTTGTGCG ATGGACAAGA TTATGACGAA GTATATCTTG CAGGCAGCTG

101 GGATTCCACA AGTACCTTAT GTACCGGTGT TAAAGAATCA ATGGAAAGAA

151 AACCCTAAAC AAGTTTTTGA TAAATGTGAA GGAACCTTGT TGTATCCAAT

201 GTTTATCAAA CCAGCGAATA TGGGTTCTAG CGTCGGAATT AGCCGCGCTG

251 AGAATCGCGA AGAACTACAA AATGCCTTGA AAGAAGCCTA TCGGTATGAT

301 TCGCGGGCAT TAGTTGAACA AGGAATCGAT GCTCGTGAAA TTGAGGTTGC

351 CGTTTTAGGC AACGATGACG TTCGAACAAC GTTGCCTGGC GAAGTCGTGA

401 AGGAAGTAGC CTTCTATGAT TACAATGCTA AGTACATCGA TAATACGATT

451 CAAATGGCGA TTCCAGCAGA AGTGCCGAAA GAAGTGATGC AAAAAGCTCG

501 GGAGTATGCA AAATTAGCTT CACGATGTT AGGCGGATCG GGCTTGAGCC

551 GTTGCGACTT CTTTTTGACC AATAAAAATG AATTATTCTT AAATGAGTTA

SEQ ID NO: 28
Enterococcus cecorum D-alanine:
D-alanine ligase gene, partial cds.
    1 TTTTTAGAAA CTTTGAAGAT GCCTTATGTC GGTACAGGGG TTTTAGCAAG

51 TGCGTGTGGC ATGGATAAAA TTATGACCAA ATATGTCTTA CAAGCAGGTG

101 GCATCCCACA AGTGCCTTAT GTTCCGGTAT TAGCCATGCA TTGGAAACAA

151 GATCCACAAT TAATCTTTGA ACATTGCGAA GGTTCCTTAT TATACCCAAT
```

```
    201 GTTTGTCAAA CCGGCGAATA TGGGTTCAAG CGTGGGAATT TCTAAGGCTG

251 AAAACCGTGA TGAATTAGAA GCAGCTTTAA ATGAAGCATT CTTATATGAT

301 ACACGCGGGA TTATCGAGCA AGGAATTGAA GTTGCTGTTT TAGAAATGAA

351 GAATGTTCGT ACGACTATGG CGGGTGAAAT TGTTAAAGAT GTCGCTTTTT

401 ACGATTATAA TTCAAAATAT ATCGACAACA AAATTGTGAT GCAAATCCCG

451 GCACAAGTAC CTGATGAAGT GCAACAAAAA GCACAAGAAT ATGCCAAAAA

501 AGCTTATACC ATGCTTGGTG GCTCAGGATT AAGTCGTTGT GATTTCTTCT

551 TAACCAATAA GAACGAATTA TTCTTAAATG AATTA

SEQ ID NO: 29
Enterococcus saccharolyticus D-alanine:
D-alanine ligase gene, partial cds.
      1 TTCCTTGAAA CCATTCGTAT GCCGTATGTG GGTGCCGGTG TCTTAACAAG

51 TGCCTGTGGA ATGGATAAGA TTATGACAAA ATATATCTTA CATTCAGCTG

101 GAATTCCACA AGTTCCTTAT GTACCCGTGT TGAAAAATCA ATGGAAAGAA

151 AATCCAAAAC AAATTTTTGA ACAATGTGAA GGCTCTCTAC GTTACCCAAT

201 GTTTGTTAAG CCAGCGAATA TGGGATCAAG TGTAGGCATT TCAAAAGCCG

251 AAAATCGCGT CGAGCTGCAA AATGCATTAG AAGAAGCTTA CAAGTATGAT

301 AACCGTGCAG TGATTGAGCA GGGCATTGAA GCACGTGAAA TCGAAGTAGC

351 GATTTTAGGG AATGAAGATG TTCGTACAAC GATGGCGGGC GAAATTGTTA

401 AAGATGTGGC GTTTTATGAT TATAATTCAA AATATATCGA TAACAGTATT

451 GTGATGCAAA TTCCAGCACA AGTTCCTGAT GAAGTGCAAG AAAAAGCACA

501 AGAATATGCC AAACTTGCTT ATACGATGTT AGGTGGAAGT GGATTAAGCC

551 GTTGTGATTT CTTTTTAACA AATAAAAATG AATTATTCTT AAATGAATTA

SEQ ID NO: 30
Enterococcus dispar D-alanine:
D-alanine ligase gene, partial cds.
      1 TTCTTAGAAA CCATTGATAT GCCTTATATT GGGGCGGGAG TTTTAACAAG

51 TGCTTGTGGC ATGGATAAAA TCATGACCAA ATATATTCTA CAAGCTGCGG

101 GTATTCCACA AGTACCTTAT GTGCCAGTCT TGAAAAATCT GTGGAAAGAA

151 AATCCTAAAC AAATTTTTGA GCAATGTGAA GGAACTCTGT ATACCCAAT

201 GTTTGTTAAG CCAGCCAACA TGGGTTCTTC TGTCGGCATT TCAAAAGCTG

251 AAAACAGAGA AGAATTGCAA AATGCATTGC AAGAAGCGTA TAAATATGAC

301 ACGCGGGCAA TTGTCGAACA AGGAATTGAA CGCGGGGAAA TTGAAGTTGC

351 AATTTTAGGT AACGAAGATG TTCGGACTAC TTTACCTGGT GAAATTGTAA

401 AAGATGTCGC TTTTTATGAC TATAATTCCA AATATATCGA CAACCAAATT

451 ATCATGCAGA TTCCGGCTGA ATACCAGAA GACGTACAAC AAAAAGCACA

501 AGATTTTGCT AAAAAAGCCT ACGTTATGCT AGGTGGAAGT GGCTTGTCGC

551 GTTGTGATTT CTTTTTAACG AATAAAAATG AATTGTTCTT AAATGAATTA

SEQ ID NO: 31
Enterococcus hirae D-alanine:
D-alanine ligase gene, complete cds.
      1 GGGAGCACAA TCTTTTGAAG ATTACTTTAC TATATGGTGG ACGCAGTGCA

51 GAACATGATG TTTCAGTTCT TTCAGCGTTT TCAGTCTTAA ATGCTATTTA
```

-continued

```
 101 TTATACGTAC TATCAAGTTC AACTGATATT TATCAGCAAA GAAGGTCAAT

151 GGGTGAAAGG CCCTTTGTTA ACAGAGAAAC CAACGAGCAA AGAAGACTTA

201 CATTTGACAT GGGACCCAAG CGGAAAAGTG ACAGATGGCT TTACGGGAAG

251 AGTGATCAAT CCTGGAGAAA TCAAAGAAGA AGGAACGATT GTTTTCCCTG

301 TCTTACACGG ACCTAATGGT GAAGATGGAA CGATTCAAGG ATTTTTGGAA

351 ACATTGAACT TGCCATATGT CGGCGCTGGC GTTTTAACAA GTGCTTGTGC

401 AATGGATAAG ATCATGACCA ATACATTTT GCAAGCGGCA GGGGTGCCAC

451 AAGTTCCTTA TGTCCCTGTT TTGAAAAATC AATGGAAAGA AAATCCTAAA

501 AAAATCTTTG ATCAATGTGA AGGGTCTTTG CTTTACCCAA TGTTTGTCAA

551 ACCAGCAAAT ATGGGTTCAA GTGTAGGGAT CTCTAAAGCG GAGAACCGTG

601 AAGAACTGCA AAATGCGCTT GCATTAGCTT ATCAATATGA TTCTCGTGCG

651 ATCGTTGAGC AAGGGATCGA AGCACGTGAA ATTGAAGTAG CTGTTTTAGG

701 GAATGAAGAC GTGCGTACCA CATTACCTGG TGAAGTAGTC AAAGATGTTG

751 CATTCTATGA TTATGATGCG AAATACATCA ACAATAAGAT TGAAATGCAA

801 ATCCCAGCTG AAGTACCGGA AGAGGTCTAT CAAAAAGCGC AGGAATATGC

851 AAAAATTGCG TATACAATGC TAGGTGGGAG TGGCTTGAGC CGTTGTGATT

901 TCTTCTTGAC GAATAAAAAT GAACTATTCC TAAATGAGTT AAATACAATG

951 CCTGGATTCA CGCAATTTAG CATGTATCCA TTATTGTGGG AAAACATGGG

1001 CTTGAAGTAT GGCGATTTGA TCGAAGAATT GATTCAATTA GGAATCAATC

1051 GTTTTAATCA ACGACAAGGT TTTTTTAACG CAAACGAATA GACAA
```

SEQ ID NO: 32
Enterococcus gallinarum D-alanine:
D-alanine ligase gene, partial cds.

```
   1 AAATGTGGAA GAATTAGTTT TGGTAGAAAC AATGAATACA GGAGGAATTT

51 CTTTTGAAAA TTATTTTATT ATATGGCGGA CGCAGTGCAG AGCATGATGT

101 ATCGCTTCTA TCCGCTTTTT CAGTAGTCAA TGCTGTATAT TATAATTACT

151 ACCAAGTACA ATTAGTAATG ATCACGAGAG ATGGCCAGTG GCTAAAAGGC

201 TCTTTATTGA CTGAAGCCCC TACATCCAAA GAAGTGTTGA ATCTGACGGA

251 TTCGGCTTAC CAAGGGACGC CGATCCAACC TGGTGAGATC AAGGAAGAGG

301 ATGCGATTGT TTTTCCGCTG CTCCACGGAC CAAATGGAGA AGATGGAACG

351 ATCCAAGGTT TTCTAGAGAC CATCGGCATG CCTTATGTAG CGCAGGGGT

401 TTTAACTAGT GCCTGTGGCA TGGATAAGAT TATGACCAAA TATATCTTGC

451 AGGCGGCGGG GATTCCGCAA GTTCCTTATG TACCCGTTCT TAAAAACTAT

501 TGGAAAGAAA ATCCTAAAAA AGTATTTGAA CAATGTGAAG GCAGTCTTTT

551 GTATCCAATG TTTATCAAAC CTGCCAATAT GGGTTCAAGT GTTGGGATCA

601 CAAAAGCTGA AAATCGGGAA GAATTGCAAA ATGCACTTCA AGAAGCCTAC

651 CGTTATGATA CACGAGCGAT CGTAGAACAA GGGATCGAAG CTCGCGAAAT

701 CGAAGTCGCT GTTCTTGGAA ATGAAGATGT GCGTACAACA ATGCCCGGCG

751 AGATCGTTAA AGATGTAGCT TTTTATGATT ACAATTCGAA GTATCTTGAC

801 AATAAGATTG AGATGCAGAT CCCAGCTCAA ATTCCTGAGG AGACACAAGC

851 GAAAGCGCAA GAGTTTGCCA AAAAAGCTTA TACGATGCTT GGAGGAAGCG
```

```
-continued
 901 GCCTCAGCCG CTGCGACTTT TTCTTGACGA ACAAAAACGA ATTATTCCTG

951 AATGAATTGA ACACCATCCC CGCTTTACAA GCCGAATTCT GCAGATATCC

1001 A

SEQ ID NO: 33
Enterococcus faecium putative D-alanine:
D-alanine ligase gene, partial cds.
   1 TTCTTAGAGA CATTGAATAT GCCTTATGTC GGCGCAGGCG TATTGACCAG

51 TGCATGTGCC ATGGATAAAA TCATGACCAA GTATATTTTA CAAGCTGCTG

101 GTGTGCCGCA AGTTCCTTAT GTACCAGTAC TTAAGAATCA ATGGAAAGAA

151 AATCCTAAAA AAGTATTTGA TCAATGTGAA GGTTCTTTGC TTTATCCGAT

201 GTTTGTCAAA CCTGCGAATA TGGGTTCTAG TGTCGGCATT ACAAAGGCAG

251 AAAACCGAGA AGAGCTGCAA AATGCTTTAG CAACAGCCTA TCAGTATGAT

301 TCTCGAGCAA TCGTTGAACA AGGAATTGAA GCGCGCGAAA TCGAAGTTGC

351 TGTATTAGGA AATGAAGATG TTCGGACGAC TTTGCCTGGC GAAGTCGTAA

401 AAGACGTAGC ATTCTATGAT TATGAAGCCA AATATATCAA TAATAAAATC

451 GAAATGCAGA TTCCAGCCGA AGTGCCGGAA GAAGTTTATC AAAAAGCGCA

501 AGAGTACGCG AAGTTAGCTT ACACGATGTT AGGTGGAAGC GGATTGAGCC

551 GGTGCGATTT CTTTTTGACA AATAAAAATG AATTATTCCT GAATGAATTA
```

The above-described purified polynucleotides from Enterococci have been selected from the sequences of the ddl genes from eight isolates of Enterococci, the amino acid sequences of which are described in Evers et al. (J. Mol. Evol., 1996, 42:706–712). The Evers et al. article was made available to the public on Jun. 27, 1996.

More particularly, the degenerate pair of primers V1 and V2 have been used to amplify polynucleotides corresponding to the ddl gene of various Streptococci and Enterococci strains. The resulting nucleotide sequences have been aligned. Then, the non-conserved regions of the ddl gene sequences were identified and have been used as polynucleotides that hybridize specifically with the nucleic acid molecules from a particular strain of a bacterium belonging to the Streptococci or to the Enterococci genus.

Accordingly, this invention provides specific pairs of oligonucleotide primers as well as their use to amplify nucleic acid (RNA or DNA) from particular strains of the Streptococci genus. As a specific embodiment of pairs of primers specific for Streptococci are the oligonucleotides described in the Example herein. These primers are specific for particular species or groups of species of Streptococci, and in particular of the viridans group of species.

The polynucleotides from Streptococci internal to the portion of the ddl gene amplified with the V1/V2 pair of primers have been inserted in vectors that are contained in the E. coli strains deposited at the Collection Nationale de Cultures de Microorganismes ("CNCM"), Institut Pasteur, 28, Rue du Docteur Roux, F-75724 Paris Cedex 15, France, on Mar. 7, 1997, and which are referred to herein by the following accession numbers:

| Plasmid | Accession No. |
|---------|---------------|
| pAT 438 | I-1854 |
| pAT 439 | I-1855 |
| pAT 440 | I-1856 |
| pAT 441 | I-1857 |
| pAT 442 | I-1858 |
| pAT 443 | I-1859 |
| pAT 444 | I-1860 |
| pAT 445 | I-1861 |
| pAT 446 | I-1862 |

Another embodiment of the purified polynucleotides according to the present invention provides polynucleotides useful as primers or probes that hybridize specifically, under stringent hybridization conditions as defined hereinafter, to the nucleic acid (RNA or DNA) from particular species of the Enterococci genus.

In a specific embodiment of the present invention, the purified polynucleotides useful for detecting Streptococci and the purified polynucleotides useful for detecting Enterococci may be used in combination in order to detect simultaneously the presence of bacteria belonging to Streptococci and Enterococci in a biological sample. Thus, the present invention also provides detection methods and kits comprising combinations of the purified polynucleotides according to the invention. The purified oligonucleotides of the invention are also useful as primers for use in amplification reactions or as nucleic acid probes.

Thus, the polynucleotides of SEQ ID Nos. 1 to 16 as well as the polynucleotides of SEQ ID No. 17 to 25 and polynucleotides of SEQ ID Nos. 26–33 and their fragments can be used to select nucleotide primers notably for an amplification reaction, such as the amplification reactions further described.

PCR is described in the U.S. Pat. No. 4,683,202 granted to Cetus Corp. The amplified fragments may be identified by agarose or polyacrylamide gel electrophoresis, or by a capillary electrophoresis, or alternatively by a chromatography technique (gel filtration, hydrophobic chromatography, or ion exchange chromatography). The specificity of the amplification can be ensured by a molecular hybridization using as nucleic probes the polynucleotides of SEQ ID Nos. 1 to 16 as well as the polynucleotides of SEQ ID Nos. 17 to 25 and polynucleotides of SEQ ID Nos. 26–33 and their fragments, oligonucleotides that are complementary to these polynucleotides or fragment thereof, or their amplification products themselves.

Amplified nucleotide fragments are useful as probes in hybridization reactions in order to detect the presence of one polynucleotide according to the present invention or in order to detect the presence of a bacteria of the Streptococci or of the Enterococci genus in a biological sample. This invention also provides the amplified nucleic acid fragments ("amplicons") defined herein above. These probes and amplicons can be radioactively or non-radioactively labeled, using for example enzymes or fluorescent compounds.

Preferred nucleic acid fragments that can serve as primers according to the present invention are the following:

polynucleotides of sequence SEQ ID Nos. 1 to 16; and polynucleotides having a length from 12 to 50 consecutive nucleotides from a polynucleotide selected from the group consisting of polynucleotides of sequences SEQ ID No. 17 to SEQ ID No. 25.

The primers can also be used as oligonucleotide probes to specifically detect a polynucleotide according to the invention.

Other techniques related to nucleic acid amplification can also be used and are generally preferred to the PCR technique. The Strand Displacement Amplification (SDA) technique (Walker et al., 1992) is an isothermal amplification technique based on the ability of a restriction enzyme to cleave one of the strands at a recognition site (which is under a hemiphosphorothioate form), and on the property of a DNA polymerase to initiate the synthesis of a new strand from the 3' OH end generated by the restriction enzyme and on the property of this DNA polymerase to displace the previously synthesized strand being localized downstream. The SDA method comprises two main steps:

a) The synthesis, in the presence of dCTP-alpha-S, of DNA molecules that are flanked by the restriction sites that may be cleaved by an appropriate enzyme.

b) The exponential amplification of these DNA molecules modified as such, by enzyme cleavage, strand displacement, and copying of the displaced strands. The steps of cleavage, strand displacement, and copying are repeated a sufficient number of times in order to obtain accurate sensitivity of the assay.

The SDA technique was initially realized using the restriction endonuclease HincII, but is now generally practiced with an endonuclease from *Bacillus stearothermophilus* (BsoBI) and a fragment of a DNA polymerase, which is devoid of any 5'→3' exonuclease activity isolated from *Bacilllus cladotenax* (exo-Bca). Both enzymes are able to operate at 60° C., and the system is now optimized in order to allow the use of dUTP and the decontamination by UDG. When using this technique, as described by Spargo et al. in 1996, the doubling time of the target DNA is of the order of 26 seconds, and the amplification rate is of the order of $10^{10}$ after an incubation time of 15 min at 60° C.

The SDA amplification technique is more easy to perform than PCR (a single thermostated water bath device is necessary), and is faster than the other amplification methods. Thus, the present invention also comprises using the nucleic acid fragments according to the invention (primers) in a method of DNA or RNA amplification according to the SDA technique. For performing SDA, two pairs of primers are used: a pair of external primers (B1, B2) comprising a sequence specific to the target polynucleotide of interest, and a pair of internal primers (S1, S2) comprising a fusion oligonucleotide carrying a site that is recognized by a restriction endonuclease, for example the enzyme BsoBI.

As an illustrative embodiment of the use of the primers according to the invention in SDA amplification, a sequence that is non-specific for the target polynucleotide and carrying a restriction site for HincII or BsoBI is added at the 5' end of a primer according to the present invention. Such an additional sequence containing a restriction site that is recognized by BsoBI is advantageously the following sequence

SEQ ID NO:34 GCATCGAATGCATGTCTCGGGT the nucleotides represented in bold characters corresponding to the recognition site of the enzyme BsoBI. Thus, primers useful for performing SDA amplification can be designed from any of the primers according to the invention as described above and are part of the present invention. The operating conditions to perform SDA with such primers are described in Spargo et al, 1996. More specifically, the following conditions can be employed when preforming the SDA amplification reaction with the primers of the invention designed to contain a BsoBI restriction site:

BsoBI/exo⁻Bca [=exo-minus-Bca] SDA reactions are performed in a 50 µl volume with final concentrations of 9.5 mM $MgCl_2$, 1.4 mM each dGTP, dATP, TTP, dCTP-alpha-S, 100 µg/ml acetylated bovine serum albumin, 10 ng/ml human placental DNA, 35 mM $K_2HPO_4$ pH 7.6, 0.5 µM primers $S1_{BsoBI}$ and $B2_{BsoBI}$, 0.05 µM primers $B1_{BsoBI}$ and $B2_{BsoBI}$, 3.2 U/µl BsoBI enzyme, 0.16 U/µl exo⁻Bca enzyme, 3 mM Tris-HCl, 11 mM NaCl, 0.3 mM DTT, 4 mM KCl, 4% glycerol, 0.008 mM EDTA, and varying amounts of target DNA. Prior to the addition of BsoBI and exo⁻Bca, incomplete reactions (35 µl) are heated at 95° C. for 3 min to denature the target DNA, followed by 3 min at 60° C. to anneal the primers. Following the addition of a 15 µl enzyme mix consisting of 4 µl of BsoBI (40 Units/µl), 0.36 µl exo⁻Bca (22 Units/µl), and 10.6 µl enzyme dilution buffer (10 mM Tris Hcl, 10 mM $MgCl_2$, 50 mM NaCl, 1 mM DTT), the reactions are incubated at 60° C. for 15 min. Amplification is terminated by heating for 5 min in a boiling water bath. A no-SDA sample is created by heating a sample in a boiling water bath immediately after enzyme addition. Aerosol resistant tips from Continental Laboratory Products are used to reduce contamination of SDA reactions with previously amplified products.

The polynucleotides of SEQ ID Nos. 1 to 16 as well as the polynucleotides of SEQ ID Nos. 17 to 25 and polynucleotides of SEQ ID Nos. 26 to 33 and their fragments, especially the primers according to the invention, are useful as technical means for performing different target nucleic acid amplification methods such as:

TAS (Transcription-based Amplification System), described by Kwoh et al. in 1989;

SR (Self-Sustained Sequence Replication), described by Guatelli et al. in 1990;

NASBA (Nucleic acid Sequence Based Amplification), described by Kievitis et al. in 1991; and TMA (Transcription Mediated Amplification).

The polynucleotides of SEQ ID Nos. 1 to 16 as well as the polynucleotides of SEQ ID Nos. 17 to 25 and polynucleotides of SEQ ID Nos. 26 to 33 and their fragments, especially the primers according to the invention, are also useful as technical means for performing methods for amplification or modification of a nucleic acid used as a probe, such as:

LCR (Ligase Chain Reaction), described by Landegren et al. in 1988 and improved by Barany et al. in 1991, who employ a thermostable ligase;

RCR (Repair Chain Reaction), described by Segev et al. in 1992;

CPR (Cycling Probe Reaction), described by Duck et al. in 1990; and

Q-beta replicase reaction, described by Miele et al. in 1983 and improved by Chu et al. in 1986, Lizardi et al. in 1988, and by Burg et al. and Stone et al. in 1996.

When the target polynucleotide to be detected is RNA, for example mRNA, a reverse transcriptase enzyme can be used before the amplification reaction in order to obtain a cDNA from the RNA contained in the biological sample. The generated cDNA can be subsequently used as the nucleic acid target for the primers or the probes used in an amplification process or a detection process according to the present invention.

Nucleic probes according to the present invention are specific to detect a polynucleotide of the invention. By "specific probes" according to the invention is meant any oligonucleotide that hybridizes with one polynucleotide of SEQ ID Nos. 1 to 33 and which does not hybridize with unrelated sequences. Preferred oligonucleotide probes according to the invention are at least 12 nucleotides in length, and more preferably a length comprised between 12 and 1095 nucleotides, more preferably from 12 and 200 nucleotides, and most preferably from 12 to 50 nucleotides.

In a specific embodiment, the purified polynucleotides according to the present invention encompass polynucleotides having at least 80% homology in their nucleic acid sequences with polynucleotides of SEQ ID No. 1 to 33. By percentage of nucleotide homology according to the present invention is intended a percentage of identity between the corresponding bases of two homologous polynucleotides, this percentage of identity being purely statistical and the differences between two homologous polynucleotides being located at random and on the whole length of said polynucleotides.

The oligonucleotide probes according to the present invention hybridize specifically with a DNA or RNA molecule comprising all or part of one polynucleotide among SEQ ID Nos. 1 to 33 under stringent conditions. As an illustrative embodiment, the stringent hybridization conditions used in order to specifically detect a polynucleotide according to the present invention are advantageously the following:

Prehybridization and hybridization are performed at 68° C. during 3 to 18 hours in:

0.1% sodium dodecyl sulfate (SDS);

0.05% nonfat dry milk; and

6× SSC (1× SSC is 0.15 M NaCl plus 0.015 M sodium citrate).

The washings are performed as follows:

Two washings at laboratory temperature during 30 min. in the presence of 2× SSC and 0.1% SDS; and Two washings at 68° C. during 45 min. in the presence of 0.2× SSC and 0.1% SDS.

The non-labeled polynucleotides or oligonucleotides of the invention can be directly used as probes. Nevertheless, the polynucleotides or oligonucleotides are generally labeled with a radioactive element ($^{32}$P, $^{35}$S, $^{3}$H, $^{125}$I) or by a non-isotopic molecule (for example, biotin, acetylaminofluorene, digoxigenin, 5-bromodesoxyuridin, fluorescein) in order to generate probes that are useful for numerous applications. Examples of non-radioactive labeling of nucleic acid fragments are described in the French Patent No. FR-7810975 or by Urdea et al. or Sanchez-Pescador et al. 1988.

Other labeling techniques can also be used, such as those described in the French patents 2 422 956 and 2 518 755. The hybridization step may be performed in different ways (Matthews et al. 1988). A general method comprises immobilizing the nucleic acid that has been extracted from the biological sample on a substrate (nitrocellulose, nylon, polystyrene) and then incubating, in defined conditions, the target nucleic acid with the probe. Subsequent to the hybridization step, the excess amount of the specific probe is discarded, and the hybrid molecules formed are detected by an appropriate method (radioactivity, fluorescence, or enzyme activity measurement).

Advantageously, the probes according to the present invention can have structural characteristics such that they allow signal amplification, such structural characteristics being, for example, branched DNA probes as those described by Urdea et al. in 1991 or in the European Patent No. 0 225 807 (Chiron).

In another advantageous embodiment of the probes according to the present invention, the probes can be used as "capture probes", and are for this purpose immobilized on a substrate in order to capture the target nucleic acid contained in a biological sample. The captured target nucleic acid is subsequently detected with a second probe, which recognizes a sequence of the target nucleic acid that is different from the sequence recognized by the capture probe.

The oligonucleotide fragments useful as probes or primers according to the present invention are polynucleotides of SEQ ID Nos. 1 to 33. Said probes or primers also can be prepared by cleavage of the polynucleotides of SEQ ID Nos. 17 to 33 by restriction enzymes, as described in Sambrook et al. in 1989. Another appropriate preparation process of the nucleic acids of the invention containing at most 200 nucleotides (or 200 bp if these molecules are double-stranded) comprises the following steps:

synthesizing DNA using the automated method of beta-cyanethylphosphoramidite described in 1986;

cloning the thus obtained nucleic acids in an appropriate vector; and purifying the nucleic acid by hybridizing to an appropriate probe according to the present invention.

A chemical method for producing the nucleic acids according to the invention, which have a length of more than 200 nucleotides (or 200 bp if these molecules are double-stranded) comprises the following steps:

Assembling the chemically synthesized oligonucleotides, having different restriction sites at each end;

cloning the thus obtained nucleic acids in an appropriate vector; and purifying the nucleic acid by hybridizing to an appropriate probe according to the present invention.

The oligonucleotide probes according to the present invention can also be used in a detection device comprising a matrix library of probes immobilized on a substrate, each probe of the matrix library being complementary to a distinct sequence of the target nucleic acid or alternatively being complementary to distinct target nucleic acid.

Optionally, the substrate of the matrix can be a material able to act as an electron donor, the detection of the matrix positions in which hybridization has occurred being subsequently determined by an electronic device. Such matrix libraries of probes and methods of specific detection of a target nucleic acid are described in the European patent application No. 0 713 016, or 401 Application No. WO 95 33846, or also 401 Application No. WO 95 11995 (Affymax Technologies), 401 Application No. WO 97 02357 (Affymetrix Inc.), and also in U.S. Pat. No. 5,202,231 (Drmanac), said patents and patent applications being herein incorporated by reference.

The present invention also pertains to a family of recombinant plasmids containing at least a nucleic acid according to the invention. According to an advantageous embodiment, a recombinant plasmid comprises a polynucleotide of SEQ ID Nos. 1 to 33 or one nucleic fragment of a polynucleotide of SEQ ID Nos. 17 to 33. More specifically, the following plasmids are part of the invention: pAT 438; pAT 439; pAT 440; pAT 441; pAT 442; pAT 443; pAT 444; pAT 445; and pAT 446, and also pAT 409; pAT 412; pAT 410; pAT 413; pAT 411; pAT 405; pAT 408; and pAT 406.

The present invention is also directed to the full length coding sequences of the ddl genes from Streptococci that are available using the purified polynucleotides according to the present invention, as well as to the polypeptide enzymes D-Ala:D-Ala ligase encoded by these full length coding sequences. In a specific embodiment of the present invention, the full length coding sequences of the ddl genes are isolated from a plasmid or cosmid library of the genome of Streptococci (and Enterococci) that have been screened with the oligonucleotide probes according to the present invention. The selected positive plasmid or cosmid clones hybridizing with the oligonucleotide probes of the invention are then sequenced in order to characterize the corresponding full length coding sequence, and the DNA insert of interest is then cloned in an expression vector in order to produce the corresponding D-Ala:D-Ala ligase. A suitable method for obtaining the full length coding sequences using the polynucleotides according to the present invention as a starting material is described in Sambrook et al. (1989), which is incorporated herein by reference.

In still another embodiment, this invention provides polynucleotides of Enterococci species, including:

```
Enterococcus avium D-alanine:
D-alanine ligase gene, partial cds.
    1 TTCTTAGAGA CATTGGATAT GCCTTACGTT GGTGCGGGTG TAATGACGAG  [SEQ ID NO. 26]

51 TGCTTGTGCA ATGGACAAAA TTATGACGAA ATACATTTTG CAGGCAGCTG

101 GCATCCCGCA GGTTCCTTAC GTTCCAGTCC TAAAAAACCA ATGGAAAGAA

151 AATCCTAAAC AAATTTTTGA TAAATGTGAG GGAACGTTAC TGTATCCAAT

201 GTTTGTCAAA CCGGCGAATA TGGGCTCTAG CGTAGGAATT TCACGTGCTG

251 AAAATCGCGA AGAACTGCAA AACGCATTGC AAGAAGCTTA TCGCTATGAT

301 TCAAGAGCTT TAGTTGAGCA AGGCATCGAT GCTTGTGAGA TTGAAGTTGC

351 GGTTTTAGGC AATGACGATG TGCGGACGAC ATTACCTGGT GAGGTCGTAA

401 AGGAAGAAGC ATTCTATGAT TACAATGCTA AATACATCAA TAATACGATT

451 CAAATGGCAA TTCCAGCGGA TGTGCCGGAA GATGTGATGC AAAAAGCTCG

501 CGATTTTGCA AAATCAGCCA TATCAATGTT AGGTGGATCA GGATTAAGTC

551 GCTGCGACTT TTTCTTGACA AATAAAAATG AATTATTCTT GGATGAGCTG;

Enterococcus pseudoavium D-alanine:
D-alanine ligase gene, partial cds:
    1 TTTTTAGAAA CATTAGATAT GCCTTACGTA GGGGCTGGCG TGATGACTAG  (SEQ ID NO: 27)

51 TGCTTGTGCG ATGGACAAGA TTATGACGAA GTATATCTTG CAGGCAGCTG

101 GGATTCCACA AGTACCTTAT GTACCGGTGT TAAAGAATCA ATGGAAAGAA

151 AACCCTAAAC AAGTTTTTGA TAAATGTGAA GGAACCTTGT TGTATCCAAT

201 GTTTATCAAA CCAGCGAATA TGGGTTCTAG CGTCGGAATT AGCCGCGCTG

251 AGAATCGCGA AGAACTACAA AATGCCTTGA AAGAAGCCTA TCGGTATGAT

301 TCGCGGGCAT TAGTTGAACA AGGAATCGAT GCTCGTGAAA TTGAGGTTGC

351 CGTTTTAGGC AACGATGACG TTCGAACAAC GTTGCCTGGC GAAGTCGTGA

401 AGGAAGTAGC CTTCTATGAT TACAATGCTA AGTACATCGA TAATACGATT

451 CAAATGGCGA TTCCAGCAGA AGTGCCGAAA GAAGTGATGC AAAAAGCTCG

501 GGAGTATGCA AAATTAGCTT ACACGATGTT AGGCGGATCG GGCTTGAGCC
```

```
551 GTTGCGACTT CTTTTTGACC AATAAAAATG AATTATTCTT AAATGAGTTA;
```

Enterococcus cecorum D-alanine:
D-alanine ligase gene, partial cds:

```
  1 TTTTTAGAAA CTTTGAAGAT GCCTTATGTC GGTACAGGGG TTTTAGCAAG  [SEQ ID NO. 28]

51 TGCGTGTGGC ATGGATAAAA TTATGACCAA ATATGTCTTA CAAGCAGGTG

101 GCATCCCACA AGTGCCTTAT GTTCCGGTAT TAGCCATGCA TTGGAAACAA

151 GATCCACAAT TAATCTTTGA ACATTGCGAA GGTTCCTTAT TATACCCAAT

201 GTTTGTCAAA CCGGCGAATA TGGGTTCAAG CGTGGGAATT TCTAAGGCTG

251 AAAACCGTGA TGAATTAGAA GCAGCTTTAA ATGAAGCATT CTTATATGAT

301 ACACGCGGGA TTATCGAGCA AGGAATTGAA GTTGCTGTTT TAGAAATGAA

351 GAATGTTCGT ACGACTATGG CGGGTGAAAT TGTTAAAGAT GTCGCTTTTT

401 ACGATTATAA TTCAAAATAT ATCGACAACA AAATTGTGAT GCAAATCCCG

451 GCACAAGTAC CTGATGAAGT GCAACAAAAA GCACAAGAAT ATGCCAAAAA

501 AGCTTATACC ATGCTTGGTG GCTCAGGATT AAGTCGTTGT GATTTCTTCT

551 TAACCAATAA GAACGAATTA TTCTTAAATG AATTA;
```

Enterococcus saccharolyticus D-alanine:
D-alanine ligase gene, partial cds:

```
  1 TTCCTTGAAA CCATTCGTAT GCCGTATGTG GGTGCCGGTG TCTTAACAAG  [SEQ ID NO. 29]

51 TGCCTGTGGA ATGGATAAGA TTATGACAAA ATATATCTTA CATTCAGCTG

101 GAATTCCACA AGTTCCTTAT GTACCCGTGT TGAAAAATCA ATGGAAAGAA

151 AATCCAAAAC AAATTTTTGA ACAATGTGAA GGCTCTCTAC GTTACCCAAT

201 GTTTGTTAAG CCAGCGAATA TGGGATCAAG TGTAGGCATT TCAAAAGCCG

251 AAAATCGCGT CGAGCTGCAA AATGCATTAG AAGAAGCTTA CAAGTATGAT

301 AACCGTGCAG TGATTGAGCA GGGCATTGAA GCACGTGAAA TCGAAGTAGC

351 GATTTTAGGG AATGAAGATG TTCGTACAAC GATGGCGGGC GAAATTGTTA

401 AAGATGTGGC GTTTTATGAT TATAATTCAA ATATATCGA TAACAGTATT

451 GTGATGCAAA TTCCAGCACA AGTTCCTGAT GAAGTGCAAG AAAAAGCACA

501 AGAATATGCC AAACTTGCTT ATACGATGTT AGGTGGAAGT GGATTAAGCC

551 GTTGTGATTT CTTTTTAACA AATAAAAATG AATTATTCTT AAATGAATTA;
```

Enterococcus dispar D-alanine:
D-alanine ligase gene, partial cds:

```
  1 TTCTTAGAAA CCATTGATAT GCCTTATATT GGGGCGGGAG TTTTAACAAG  [SEQ ID NO. 30]

51 TGCTTGTGGC ATGGATAAAA TCATGACCAA ATATATTCTA CAAGCTGCGG

101 GTATTCCACA AGTACCTTAT GTGCCAGTCT TGAAAAATCT GTGGAAAGAA

151 AATCCTAAAC AAATTTTTGA GCAATGTGAA GGAACTCTGT TATACCCAAT

201 GTTTGTTAAG CCAGCCAACA TGGGTTCTTC TGTCGGCATT TCAAAAGCTG

251 AAAACAGAGA AGAATTGCAA AATGCATTGC AAGAAGCGTA TAAATATGAC

301 ACGCGGGCAA TTGTCGAACA AGGAATTGAA CGCGGGGAAA TTGAAGTTGC

351 AATTTTAGGT AACGAAGATG TTCGGACTAC TTTACCTGGT GAAATTGTAA

401 AAGATGTCGC TTTTTATGAC TATAATTCCA AATATATCGA CAACCAAATT

451 ATCATGCAGA TTCCGGCTGA ATACCAGAA GACGTACAAC AAAAAGCACA

501 AGATTTTGCT AAAAAAGCCT ACGTTATGCT AGGTGGAAGT GGCTTGTCGC

551 GTTGTGATTT CTTTTTAACG AATAAAAATG AATTGTTCTT AAATGAATTA;
```

Enterococcus hirae D-alanine:
D-alanine ligase gene, complete cds:

```
   1 GGGAGCACAA TCTTTTGAAG ATTACTTTAC TATATGGTGG ACGCAGTGCA   [SEQ ID NO. 31]

51 GAACATGATG TTTCAGTTCT TTCAGCGTTT TCAGTCTTAA ATGCTATTTA

101 TTATACGTAC TATCAAGTTC AACTGATATT TATCAGCAAA GAAGGTCAAT

151 GGGTGAAAGG CCCTTTGTTA ACAGAGAAAC CAACGAGCAA AGAAGACTTA

201 CATTTGACAT GGGACCCAAG CGGAAAAGTG ACAGATGGCT TTACGGGAAG

251 AGTGATCAAT CCTGGAGAAA TCAAAGAAGA AGGAACGATT GTTTTCCCTG

301 TCTTACACGG ACCTAATGGT GAAGATGGAA CGATTCAAGG ATTTTTGGAA

351 ACATTGAACT TGCCATATGT CGGCGCTGGC GTTTTAACAA GTGCTTGTGC

401 AATGGATAAG ATCATGACCA ATACATTTT GCAAGCGGCA GGGGTGCCAC

451 AAGTTCCTTA TGTCCCTGTT TTGAAAAATC AATGGAAAGA AAATCCTAAA

501 AAAATCTTTG ATCAATGTGA AGGGTCTTTG CTTTACCCAA TGTTTGTCAA

551 ACCAGCAAAT ATGGGTTCAA GTGTAGGGAT CTCTAAAGCG AGAACCGTG

601 AAGAACTGCA AAATGCGCTT GCATTAGCTT ATCAATATGA TTCTCGTGCG

651 ATCGTTGAGC AAGGGATCGA AGCACGTGAA ATTGAAGTAG CTGTTTTAGG

701 GAATGAAGAC GTGCGTACCA CATTACCTGG TGAAGTAGTC AAAGATGTTG

751 CATTCTATGA TTATGATGCG AAATACATCA ACAATAAGAT TGAAATGCAA

801 ATCCCAGCTG AAGTACCGGA AGAGGTCTAT CAAAAAGCGC AGGAATATGC

851 AAAAATTGCG TATACAATGC TAGGTGGGAG TGGCTTGAGC CGTTGTGATT

901 TCTTCTTGAC GAATAAAAAT GAACTATTCC TAAATGAGTT AAATACAATG

951 CCTGGATTCA CGCAATTTAG CATGTATCCA TTATTGTGGG AAAACATGGG

1001 CTTGAAGTAT GGCGATTTGA TCGAAGAATT GATTCAATTA GGAATCAATC

1051 GTTTTAATCA ACGACAAGGT TTTTTTAACG CAAACGAATA GACAA;
```

Enterococcus gallinarum D-alanine:
D-alanine ligase gene, partial cds:

```
   1 AAATGTGGAA GAATTAGTTT TGGTAGAAAC AATGAATACA GGAGGAATTT   [SEQ ID NO. 32]

51 CTTTTGAAAA TTATTTTATT ATATGGCGGA CGCAGTGCAG AGCATGATGT

101 ATCGCTTCTA TCCGCTTTTT CAGTAGTCAA TGCTGTATAT TATAATTACT

151 ACCAAGTACA ATTAGTAATG ATCACGAGAG ATGGCCAGTG GCTAAAAGGC

201 TCTTTATTGA CTGAAGCCCC TACATCCAAA GAAGTGTTGA ATCTGACGGA

251 TTCGGCTTAC CAAGGGACGC CGATCCAACC TGGTGAGATC AAGGAAGAGG

301 ATGCGATTGT TTTTCCGCTG CTCCACGGAC AAATGGAGA AGATGGAACG

351 ATCCAAGGTT TTCTAGAGAC CATCGGCATG CCTTATGTAG GCGCAGGGGT

401 TTTAACTAGT GCCTGTGGCA TGGATAAGAT TATGACCAAA TATATCTTGC

451 AGGCGGCGGG GATTCCGCAA GTTCCTTATG TACCCGTTCT TAAAAACTAT

501 TGGAAAGAAA ATCCTAAAAA AGTATTTGAA CAATGTGAAG GCAGTCTTTT

551 GTATCCAATG TTTATCAAAC CTGCCAATAT GGGTTCAAGT GTTGGGATCA

601 CAAAAGCTGA AAATCGGGAA GAATTGCAAA ATGCACTTCA AGAAGCCTAC

651 CGTTATGATA CACGAGCGAT CGTAGAACAA GGGATCGAAG CTCGCGAAAT

701 CGAAGTCGCT GTTCTTGGAA ATGAAGATGT GCGTACAACA ATGCCCGGCG
```

-continued

```
 751 AGATCGTTAA AGATGTAGCT TTTTATGATT ACAATTCGAA GTATCTTGAC

801 AATAAGATTG AGATGCAGAT CCCAGCTCAA ATTCCTGAGG AGACACAAGC

851 GAAAGCGCAA GAGTTTGCCA AAAAAGCTTA TACGATGCTT GGAGGAAGCG

901 GCCTCAGCCG CTGCGACTTT TTCTTGACGA ACAAAAACGA ATTATTCCTG

951 AATGAATTGA ACACCATCCC CGCTTTACAA GCCGAATTCT GCAGATATCC

1001 A; and

Enterococcus faecium D-alanine:
D-alanine ligase gene, partial cds:
   1 TTCTTAGAGA CATTGAATAT GCCTTATGTC GGCGCAGGCG TATTGACCAG    [SEQ ID NO. 33]

51 TGCATGTGCC ATGGATAAAA TCATGACCAA GTATATTTTA CAAGCTGCTG

101 GTGTGCCGCA AGTTCCTTAT GTACCAGTAC TTAAGAATCA ATGGAAAGAA

151 AATCCTAAAA AAGTATTTGA TCAATGTGAA GGTTCTTTGC TTTATCCGAT

201 GTTTGTCAAA CCTGCGAATA TGGGTTCTAG TGTCGGCATT ACAAAGGCAG

251 AAAACCGAGA AGAGCTGCAA AATGCTTTAG CAACAGCCTA TCAGTATGAT

301 TCTCGAGCAA TCGTTGAACA AGGAATTGAA GCGCGCGAAA TCGAAGTTGC

351 TGTATTAGGA AATGAAGATG TTCGGACGAC TTTGCCTGGC GAAGTCGTAA

401 AAGACGTAGC ATTCTATGAT TATGAAGCCA AATATATCAA TAATAAAATC

451 GAAATGCAGA TTCCAGCCGA AGTGCCGGAA GAAGTTTATC AAAAAGCGCA

501 AGAGTACGCG AAGTTAGCTT ACACGATGTT AGGTGGAAGC GGATTGAGCC

551 GGTGCGATTT CTTTTTGACA AATAAAAATG AATTATTCCT GAATGAATTA.
```

It is now easy to produce proteins in high amounts with genetic engineering techniques by the use, as expression vectors, of plasmids, phages, or phagemids. The polynucleotides that code for the polypeptides of the present invention are inserted in an appropriate expression vector in order to in vitro produce the polypeptide of interest.

Thus, the present invention also concerns a method for producing a polypeptide of the invention, and especially a D-Ala:D-Ala ligase polypeptide of the invention. The method comprises:

a) Optionally amplifying the nucleic acid coding for the desired polypeptide using a pair of primers according to the invention (by SDA, TAS, 3SR NASBA, TMA etc.);

b) inserting the nucleic acid of interest in an appropriate vector;

c) culturing, in an appropriate culture medium, a cell host previously transformed or transfected with the recombinant vector of step b); and d) harvesting the culture medium thus conditioned, or lyse the cell host, for example, by sonication or by osmotic shock;

e) separating or purifying, from the culture medium, or from the pellet of the resultant host cell lysate, the thus produced polypeptide of interest; and f) characterizing the produced polypeptide of interest.

A suitable vector for the expression of a polypeptide according to the invention is a baculovirus vector that can be propagated in insect cells and in insect cell lines. A specific suitable host vector system is the pVL1392/1393 baculovirus transfer vector (Pharmingen) that is used to transfect the SF9 cell line (ATCC No. CRL 1711), which is derived from *Spodoptera frugiperda*. Another suitable vector for the expression in bacteria and in particular in *E. col*, is the pQE-30 vector (QIAexpress) that allows the production of a recombinant protein containing a 6xHis affinity tag. The 6xHis tag is placed at the C-terminus of the recombinant D-Ala:D-Ala ligase polypeptide, which allows a subsequent efficient purification of the recombinant D-Ala:D-Ala ligase polypeptide by passage onto a nickel or copper affinity chromatography column. The nickel chromatography column can contain the Ni-NTA resin (Porath et al. 1975).

The polypeptides according to the invention can also be prepared by conventional methods of chemical synthesis, either in a homogenous solution or in solid phase. As an illustrative embodiment of such chemical polypeptide synthesis techniques may be cited the homogenous solution technique described by Houbenweyl in 1974. The technique described by Merrifield may also be used (J. Am. Chem. Soc. 1963, 85:2149–2154).

The polypeptides according to the invention can be characterized by binding onto an immunoaffinity chromatography column on which polyclonal or monoclonal antibodies directed to a polypeptide among the D-Ala:D-Ala ligase polypeptide of the invention has previously been immobilized.

Another object of the present invention comprises a polypeptide produced by the genetic engineering techniques or a polypeptide synthesized chemically as above described.

The D-Ala:D-Ala ligase polypeptides according to the present invention are useful for the preparation of polyclonal or monoclonal antibodies that recognize the polypeptides or fragments thereof. The monoclonal antibodies can be prepared from hybridomas according to the technique described by Kohler and Milstein in 1975. The polyclonal antibodies can be prepared by immunization of a mammal, especially a mouse or a rabbit, with a polypeptide according to the invention that is combined with an adjuvant, and then by purifying specific antibodies contained in the serum of the immunized animal on a affinity chromatography column on which has previously been immobilized the polypeptide that has been used as the antigen.

Consequently, the invention is also directed to a method for detecting specifically the presence of a D-Ala:D-Ala ligase polypeptide according to the invention in a biological sample. The method comprises:

a) bringing into contact the biological sample with an antibody according to the invention; and b) detecting antigen-antibody complex formed.

Also part of the invention is a diagnostic kit for in vitro detecting the presence of a polypeptide according to the present invention in a biological sample. The kit comprises:

a polyclonal or monoclonal antibody as described above, optionally labeled; and a reagent allowing the detection of the antigen-antibody complexes formed, wherein the reagent carries optionally a label, or being able to be recognized itself by a labeled reagent, more particularly in the case when the above-mentioned monoclonal or polyclonal antibody is not labeled by itself.

Indeed, the monoclonal or polyclonal antibodies according to the present invention are useful as detection means in order to identify or characterize a particular species or group of species of Streptococci (and Enterococci).

A specific embodiment of this invention will now be described in greater detail in the following Example.

EXAMPLE

Identification to the Species Level of Clinically Relevant Viridans Group Streptococci by PCR Viridans group streptococci form an important part of the normal flora of the human oral cavity. They are responsible for several infections including purulent infections (14), endocarditis (7), septicaemia (4), and meningitis (3). Viridans streptococci do not possess a specific group antigen and show variable reactions with Lancefield antisera (11). Their identification is based on different physiological and biochemical characteristics, but conventional phenotypic identification methods are sometimes unable to differentiate established species. First, not all strains in a species may be positive for a common trait (2, 19) and, secondly the same strain may give different results on repeated tests in the absence of changes in the corresponding genes (15, 25). Thus, rapid systems using standard phenotypic tests, such as API-20STREP or rapid ID 32 Strep that are used in clinical laboratories, are not totally satisfactory for accurate identification at the species level (16, 18). Species identification of viridans streptococci is useful during the course of infective endocarditis when the patient has relapsed, in the case of positive blood cultures, and to assess the involvement of a given strain in the progress of the infection.

The polymerase chain reaction (PCR) has been extensively applied to species identification of infectious agents (8, 13, 21). PCR allows amplification of a preselected DNA region and is a highly specific and sensitive technique (20). In many instances, the target genes are involved in pathogenicity (13). In other cases, the target is a random cloned fragment from a genomic library selected by differential hybridization to the pathogen and its close relatives (23).

This study selected the ddl gene encoding a D-alanine:D-alanine (D-Ala:D-Ala) ligase, which is species specific and ubiquitous in procaryotes possessing peptidoglycan. The D-Ala:D-Ala ligase catalyses synthesis of the terminal dipeptide D-alanine—D-alanine of peptidoglycan precursors (26). A PCR assay allows identification to the species level of six species (*Streptococcus gordonii, S. mitis, S. mutans, S. oralis, S. salivarius*, and *S. sanguis*) and to the group level for three species (*S. anginosus, S. constellatus*, and *S. intermedius*), which are clinically relevant species of streptococci belonging to the viridans group.

Bacterial strains, plasmids, and culture conditions. The reference strains used were: *S. anginosus* ATCC 33397, *S. bovis* NCTC 8177, *S. constellatus* ATCC 27823, *S. gordonii* ATCC 10558, *S. intermedius* ATCC 27335, *S. mitis* NCTC 12261, *S. mutans* NCTC 10449, *S. oralis* NCTC 7864, *S. salivarius* ATCC 9758, and *S. sanguis* NCTC 7863. Ninety-one strains from the bioMérieux collection (La Balme-les-Grottes, France) were also tested: *S. anginosus* [9], *S. constellatus* [10], *S. gordonii* [10], *S. intermedius* [6], *S. mitis* [10], *S. mutans* [10], *S. oralis* [10], *S. salivarius* [10], *S. sanguis* [10], and *S. vestibularis* [6].

Plasmid PCR™II (Invitrogen, San Diego, Calif.) was used for the cloning of the PCR products. *Escherichia coli* INVαF'=One Shot™ (Invitrogen) was the host strain for recombinant plasmids. Plasmids were designated: pAT437 ($ddl_{S.\ bovis}$), pAT438 ($ddl_{S.\ gordondii}$), pAT439 ($ddl_{S.\ mitis}$), pAT440 ($ddl_{S.\ mutans}$), pAT441 ($ddl_{S.\ oralis}$), pAT442 ($ddl_{S.\ salivarius}$), pAT443 ($ddl_{S.\ sanguis}$), pAT444 ($ddl_{S.\ anginosus}$), pAT445 ($ddl_{S.\ constellatus}$), and pAT446 ($ddl_{S.\ intermedius}$).

All strains were grown at 37° C. in brain heart infusion broth and on agar (Difco Laboratories, Detroit, Mich.), supplemented or not with horse blood (5% vol/vol). For milleri group streptococci, the incubation was under anaerobic conditions.

DNA manipulation. Total DNA from streptococci was prepared by the cetyldimethylethyl-ammonium bromide method (1). Degenerate oligodeoxynucleotides

```
V1: 5'-GGX GAA GAT GGX TCX TTX CAA GGX-3'
            G   C       AG  C       G
                                A

V2: 3'-TTA TGI TAI GGI CCI AAA TG-5'
            G   A               G;
            G
``` and are complementary to sequences encoding conserved amino acid motifs in D-Ala:D-Ala ligases of *E. coli* (22, 28) and the related glycopeptide resistance enzyme VanA (9). Amplification of DNA fragments by PCR using ca. 50 ng of template DNA and primers V1 and V2 at the concentration of 0.1 μM in a total volume of 100 μl was performed on a DNA thermal cycler (model 2400; Perkin Elmer Cetus, Emeryville, Calif.) as described (10). The Taq DNA polymerase was purchased from Amersham (Amersham Life Science, Cleveland, Ohio). The PCR conditions were as follows: 94° C. for 2 min for the first cycle; 94° C. for 1 min, 54° C. for 1 min, 72° C. for 1 min for the next 30 cycles; and 72° C. for 10 min for the last cycle. The PCR products were purified by agarose gel electrophoresis followed by extraction from the cut-out low-melting agarose block using the Sephaglas™ Kit (Pharmacia, Uppsala, Sweden). Recombinant plasmids were prepared by the Wizard™ Miniprep procedure (Promega, Madison, Wis.). DNA sequence of PCR products was determined by the dideoxynucleotide chain terminator technique (24) using universal or specific oligodeoxynucleotides (Unité de Chimie Organique, Institut Pasteur, Paris, France) as primers, [α-$^{35}$S]dATP (Amersham Radiochemical Centre, Amersham, England) and T7 DNA polymerase (T7 Sequencing Kit, Pharmacia) according to the manufacturer's recommendations. For Southern hybridization, DNA was transferred by vacuum onto Nytran membranes (Schleicher and Schuell, Dassel, Germany). Prehybridization and hybridization were performed under stringent conditions at 68° C. in 0.1% sodium dodecyl sulfate (SDS)-0.05% nonfat dry milk-6× SSC (1× SSC is 0.15 M NaCl plus 0.015 M sodium citrate) during 3 and 18 hours, respectively. Probes were labeled with [α-$^{32}$P]dCTP (Amersham Radiochemical Centre) by the nick translation procedure (Nick Translation Kit, Amersham).

Sequence Analysis. Nucleotide sequences were analyzed by the Genetics Computer Group software (6) and the phylogenetic analysis performed with the PHYLIP program package (12).

GenBank Accession Numbers. The sequences were submitted to GenBank and were assigned the following accession numbers: U69162 (ddl$_{S.\ bovis}$), U69163 (ddl$_{S.\ gordonii}$), U69164 (ddl$_{S.\ mitis}$), U69165 (ddl$_{S.\ mutans}$), U69166 (ddl$_{S.\ oralis}$), U69167 (ddl$_{S.\ salivarius}$), U69168 (ddl$_{S.\ sanguis}$), U91912 (ddl$_{S.\ anginosus}$), U91913 (ddl$_{S.\ intermedius}$), and U91914 (ddl$_{S.\ constellatus}$).

Design of oligodeoxynucleotides. Internal portions (ca. 600 base pairs) of the genes coding for D-Ala:D-Ala ligases in nine species of streptococci (*S. anginosus, S. constellatus, S. gordonii, S. intermedius, S. mitis, S. mutans, S. oralis, S. salivarius,* and *S. sanguis*) were amplified by PCR using oligodeoxynucleotides V1 and V2 and cloned into the pCR™II vector. Southern hybridization with total DNA of each strain was carried out to confirm the origin of the PCR products (data not shown) that were subsequently sequenced on both strands. Sequence comparison indicated that the inserts corresponded to internal portions of ddl genes.

The partial sequences of the nine ddl genes were aligned (FIG. 1) and showed a high degree of identity. Pairs of oligodeoxynucleotides, each intended to prime amplification of a fragment internal to a ddl gene, were selected in non-conserved regions. Primers of similar size and with a GC content ranging from 43% to 60% were designed to avoid variations in annealing temperature and to allow their simultaneous use in a single reaction. However, due to the small size of the internal fragments sequenced (600 bp), the high degree of identity between the nine sequences, and the fact that each amplification product should be assigned to a species on the basis of its size, a two-step PCR appeared necessary. In the first step with pairs A to D, the amplification products obtained with pairs B and C could be assigned to a single species (Table 1). The A pair amplified *S. oralis* and *S. mitis* and the D pair both *S. gordonii* and *S. sanguis*. A second PCR using primers F and G or H and I (Table 2) allowed to differentiate *S. oralis* from *S. mitis* or *S. gordonii* from *S. sanguis*, respectively, whereas the E pair (Table 2), used alone, allowed identification of the species from the milleri group.

TABLE 1

Oligodeoxynucleotide primers for the first step PCR

| Species | Size of PCR product (bp) | Pair | Oligodeoxynucleotide Sequence | Position* | GC content (%) |
|---|---|---|---|---|---|
| S. mitis | 372 | A | 5'-GTCGAAGGTGATGATATGAC-3' | 133–152 | 50 |
| S. oralis |  |  | 3'-GACAGTACGCAGTCTTACGTC-5' | 488–508 | 52 |
| S. mutans | 351 | B | 5'-ATTGAAGGCGAGCCTTTAGAAAG-3' | 133–155 | 43 |
|  |  |  | 3'-CTAGGACAATAGCAAC-5' | 472–487 | 43 |
| S. salivarius | 331 | C | 5'-GCAGCAGTAGCAGAGACGCT-3' | 154–173 | 60 |
|  |  |  | 3'-CACGGACGTCTTCAGTACTG-5' | 469–488 | 55 |
| S. gordonii | 208 | D | 5'-GTCGATGGCGAGGATCTAGAGC-3' | 133–154 | 59 |
| S. sanguis |  |  | 3'-TGCCGAGCGCTCTAACTCCA-5' | 325–344 | 60 |

*Position was derived from the alignment in FIG. 1.

TABLE 2

Oligodeoxynucleotide primers for the second step PCR

| Group or species | Size of PCR product (bp) | Pair | Oligodeoxynucleotide Sequence | Position* | GC content (%) |
|---|---|---|---|---|---|
| A |  |  |  |  |  |
| Milleri group | 217 | E | 5'-TGCAGAAGTAGAGGCAAATC-3' | 162–181 | 45 |
|  |  |  | 3'-TTCCTCGGTTTTCGTCAACCG-5' | 362–382 | 52 |
| B |  |  |  |  |  |
| S. mitis | 259 | F | 5'-TGAAATCGAGGTTGGCCTAC-3' | 333–352 | 50 |
|  |  |  | 3'-TTCCC(G/T)CTCTAAAAGGATTTGC-5' | 571–592 | 45 |
| S. oralis | 563 | G | 5'-CTTATGTCGGCTGCAATATCC-3' | 23–43 | 47 |
|  |  |  | 3'-TTCCC(G/T)CTCTAAAAGGATTTGC-5' | 571–592 | 45 |
| C |  |  |  |  |  |
| S. gordonii | 260 | H | 5'-GTCGATGGCGAGGATCTAGAGC-3' | 133–154 | 59 |

TABLE 2-continued

Oligodeoxynucleotide primers for the second step PCR

| Group or species | Size of PCR product (bp) | Pair | Oligodeoxynucleotide Sequence | Position* | GC content (%) |
|---|---|---|---|---|---|
| | | | 3'-CAGAAGGTCCCCTTCAACAA-5' | 377–396 | 50 |
| S. sanguis | 374 | I | 5'-GTCGATGGCGAGGATCTAGAGC-3' | 133–154 | 59 |
| | | | 3'-GACTACGCAGTTTTACGTCTC-5' | 490–510 | 47 |

*Position was derived from the alignment in FIG. 1.

PCR experiments. The PCR reactions were performed with DNA from every reference strain as a template. Occurrence of nonspecific bands led us to modify the PCR conditions as follows:

94° C. for 2 min for the first cycle; 94° C. for 1 min, 56° C. for 1 min, 72° C. for 1 min for the next 20 cycles; and 72° C. for 10 min for the last cycle of the first PCR and of the second step PCR with the oligonucleotides F and G or H and I.

94° C. for 2 min for the first cycle; 94° C. for 1 min, 50° C. for 1 min, 72° C. for 1 min for the next 30 cycles; and 72° C. for 10 min for the last cycle of the PCR using the E pair.

The size of the amplification products obtained under these conditions different sufficiently to allow identification of the reference strains (data not shown).

Figure 3A:
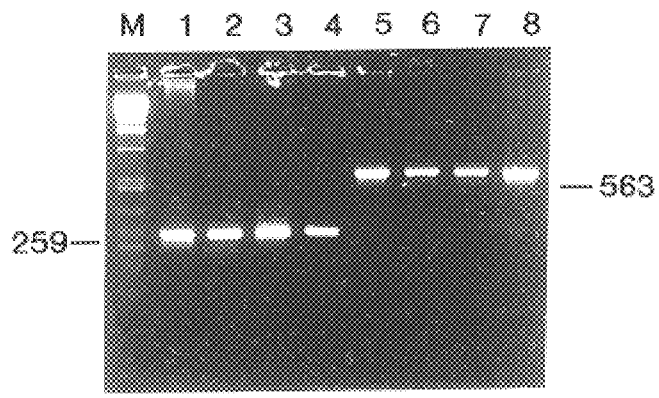
FIG. 3. Second step PCR analysis of total DNA from wild and reference strains. A. With pairs F and G; Lanes: 1, *S. mitis* NCTC 12261; 2 to 4, *S. mitis*; 5, *S. oralis* NCTC 7864; 6 to 8, *S. oralis*. B. With pairs H and I; Lanes: 1, *S. gordonii* ATCC 10588; 2 to 4, *S. gordonii*; 5, *S. sanguis* NCTC 7863; 6 to 8, *S. sanguis*. C. With pair E; Lanes: 1, *S. anginosus* ATCC 33397; 2, *S. constellatus* ATCC 27823; 3, *S. intermedius* ATCC 27335; 4 and 5, *S. anginosus*; 6 and 7, *S. constellatus*; 8 and 9, *S. intermedius*. M, bacteriophage λ DNA (Pharmacia) digested with PstI used as a size standard. PCR products were resolved by electrophoresis on a 2% agarose-Tris-borate-EDTA gel containing 0.5 µg of ethidium bromide per ml. The sizes of the PCR products are indicated in base pairs.
Figure 3B:
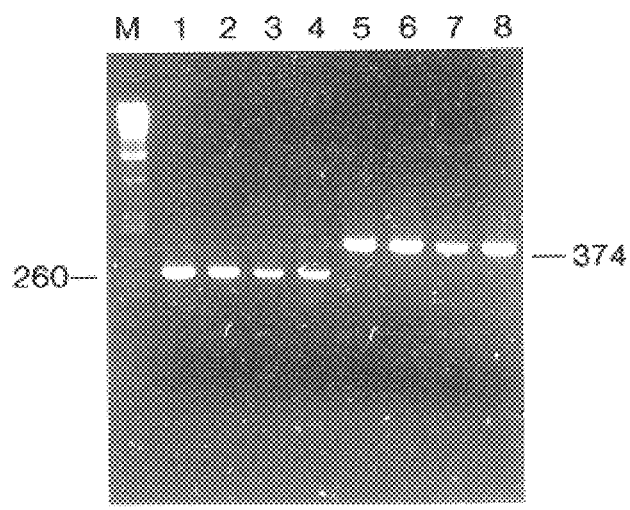
Figure 3C:
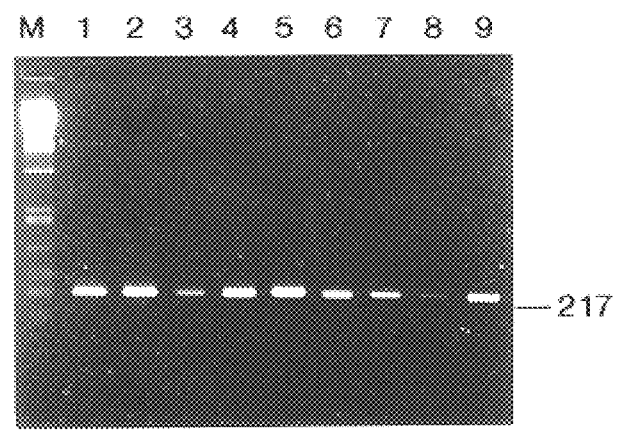

Ninety-one characterized strains of viridans group streptococci were finally investigated. PCR confirmed the identification of 60 strains [10 *S. gordonii*, 10 *S. mitis*, 10 *S. mutans*, 10 *S. oralis*, 10 *S. salivarius*, and 10 *S. sanguis*] to the species level (FIG. 2, FIGS. 3A and 3B), the assignment of 25 strains [10 *S. anginosus*, 9 *S. constellatus*, and 6 *S. intermedius*] to the milleri group (FIG. 3C), whereas the 6 strains of *S. vestibularis* were identified as *S. salivarius* (data not shown). A relatively high degree of relatedness has been observed by DNA—DNA hybridization between strains of *S. vestibularis* and *S. salivarius* (5, 27). These data are consistent with the observation that the oligonucleotides designed for *S. salivarius* amplified also a fragment from total DNA of *S. vestibularis*. However, *S. vestibularis* has not been reported to be responsible for purulent infections, endocarditis, septicaemia, or meningitis and is thus unlikely to be isolated from foci of infection.

Figure 4:
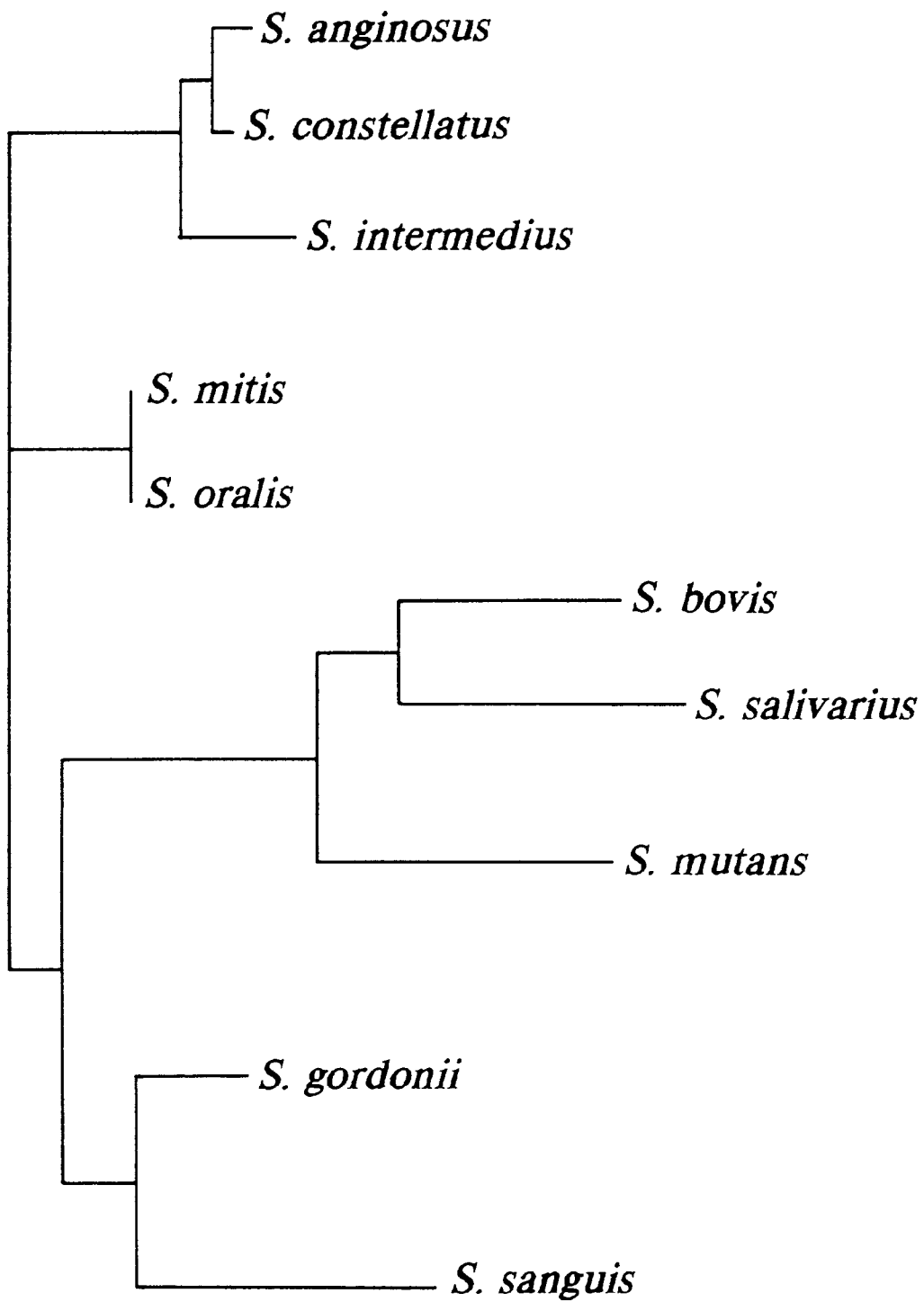
FIG. 4 shows the phylogenetic relationship among streptococci. The tree was constructed by the neighbor-joining method and slightly modified taking into account the results of maximum parsimony and bootstrapping analysis.

Phylogenetic analysis. The amino acid sequence deduced from the DNA region between oligonucleotides V1 and V2 of ten species (*S. anginosus, S. bovis, S. constellatus, S. gordonii, S. intermedius, S. mitis, S. mutans, S. oralis, S. salivarius,* and *S. sanguis*) was used for a phylogenetic analysis (FIG. 4). The phylogeny obtained was compared with that derived from 16S rRNA sequences (17). The topology of the two trees obtained with the neighbor-joining method (12) was superimposable except the difference with the nodes concerning *S. gordonil* and *S. constellatus*.

Identification to the species level of viridans group streptococci is required in certain infections. DNA—DNA hybridization with the type strain is the "gold standard" technique for identification to the species level. However, this method requires radioisotopes, involves complex procedures, and its application is thus limited to research or reference laboratories. This PCR assay provides a specific and rapid alternative to phenotypic or DNA—DNA hybridization methods for identification to the species or group level of some clinically relevant viridans group streptococci, within 48 h from the time of isolation of the organism.

A PCR assay that allows identification to the species level of clinically relevant viridans group streptococci (*Streptococcus gordonii, S. mitis, S. mutans, S. oralis, S. salivarius,* and *S. sanguis*) and to the group level for milleri group streptococci (*S. anginosus, S. constellatus,* and *S. intermedius*) was developed. This assay was based on specific amplification of internal fragments of genes encoding D-alanine:D-alanine ligases, which are species specific and ubiquitous in procaryotes possessing peptidoglycan. The specificity of the assay was tested on nine reference strains and 91 characterized clinical isolates. This assay offers a specific and rapid alternative to phenotypic or DNA—DNA hybridization methods for identification of clinically relevant viridans group streptococci.

REFERENCES

The following publications have been cited herein. The entire disclosure of each publication is relied upon and incorporated by reference herein.

Barany F., 1991, Proc. Natl. Acad. Sci. USA, 88:189–193.
Burg J. L. et al., 1996, Mol. and Cell. Probes, 10:257–271.
Chu B. C. F. et al., 1986, Nucleic Acids Res., 14:5591–5603.
Duck P. et al., 1990, Biotechniques, 9:142–147.
Guateli J. C. et al., 1990, Proc. Natl. Acad. Sci. USA, 87:1874–1878.
Houbenweyl, 1974, in Meuthode der Organischen Chemie, E. Wunsch Ed., Volume 15-I et 15-II, Thieme, Stuttgart.
Kievitis T. et al., 1991, J. Virol. Methods, 35:273–286.
Kohler G. et al., 1975, Nature, 256(5517):495–497.
Kwoh D. Y. et al., 1989, Proc. Natl. Acad. Sci. USA, 86:1173–1177.
Landegren U. et al., 1988, Science, 241:1077–1080.
Lizardi P. M. et al., 1988, Bio/technology, 6:1197–1202.
Matthews J. A. et al., 1988, Anal. Biochem., 169:1–25.
Miele et al., 1983 (J. Mol. Biol., 171 (3):281–295.
Sambrook, J. et al. 1989. In Molecular cloning : A Laboratory Manual. Cold Spring Harbor, N.Y.: Cold Spring Harbor Laboratory Press.
Sanchez-Pescador R., 1988, J. Clin. Microbiol., 26(10) :1934–1938.
Segev D., 1992, in "Non-radioactive Labeling and Detection of Biomolecules". Kessler C. Springer Verlag, Berlin, New-York, 197–205.
Spargo C. A. et al., 1996, Mol. and Cell. Probes, 10:247–256
Urdea M. S. et al., 1991, Nucleic Acids Symp. Ser., 24:197–200.
Urdea M. S., 1988, Nucleic Acids Research, 11: 4937–4957.
Walker G. T. et al., 1992, Nucleic Acids Res., 20:1691–1696.

The following additional publications have been cited in the Example. The entire disclosure of each publication is relied upon and incorporated by reference herein.

1. Ausubel, F. M., R. Brent, R. E. Kingston, D. D. Moore, J. G. Seidman, J. A. Smith, and K. Struhl, 1992. Preparation and analysis of DNA. Cur. Prot. Mol. Biol. 1:2–33.
2. Beighton, D., J. M. Hardie, and R. A. Whiley. 1991. A scheme for the identification of viridans streptococci. J. Med. Microbiol. 35:367–372.

3. Beighton, D., A. D. Carr, and B. A. Oppenheim. 1994. Identification of viridans streptococci associated with bacteriaemia in neutropenic cancer patients. J. Med. Microbiol. 40:202–204.
4. Bochud, P. -Y., Ph. Eggiman, Th. Calandra, G. Van Melle, L. Saghafi, and P. Francioli. 1994. Bacteremia due to viridans Streptococcus in neutropenic patients with cancer: Clinical spectrum and risk factors. Clin. Infect. Dis. 18:25–31.
5. Coykendall, A. L. 1989. Classification and identification of the viridans streptococci. Clin. Microbiol. Rev. 2:315–328.
6. Devereux, J., P. Haerberli, and O. Smithies. 1984. A comprehensive set of sequence analysis programs for the VAX. Nucleic Acids Res. 12:387–395.
7. Douglas, C. W. I., J. Heath, K. K. Hampton, and F. E. Preston. 1993. Identify of viridans streptococci isolated from cases of infective endocarditis. J. Med. Microbiol. 39:179–182.
8. Dutka-Malen, S., S. Evers, and P. Courvalin. 1995. Detection of glycopeptide resistance genotypes and identification to the species level of clinically relevant enterococci by PCR. J. Clin. Microbiol. 33:24–27.
9. Dutka-Malen, S., C. Molinas, M. Arthur, and P. Courvalin. 1990. The VanA glycopeptide resistance protein is related to D-alanine:D-alanine ligases cell-wall biosynthesis enzymes. Mol. Gen. Genet. 224:364–372.
10. Dutka-Malen, S., C. Molinas, M. Arthur, and P. Courvalin. 1992. Sequence of the vanC gene of *Enterococcus gallinarum* BM4174 encoding a D-alanine:D-alanine ligase-related protein necessary for vancomycin resistance. Gene 112:53–58.
11. Facklam, R. R. 1977. Physiological differentiation of viridans streptococci. J. Clin. Microbiol. 5:184–201.
12. Felsenstein, J. 1993. PHYLIP version 3.5c. University of Washington, Seattle.
13. Frankel, G., J. A. Giron, J. Valmassoi, and G. K. Schoolnik. 1989. Multi-gene amplification: simultaneous detection of three virulence genes in diarrhoeal stool. Mol. Microbiol. 3:1729–1734.
14. Gossling, J. 1988. Occurrence and pathogenicity of the *Streptococcus milleri* group. Rev. Infect. Dis. 10:257–285.
15. Hillman, J. D., S. W. Andrews, S. Painter, and P. Stashenko. 1989. Adaptative changes in a strain of *Streptococcus mutans* during colonization of the human oral cavity. Microb. Ecol. Health Dis. 2:231–239.
16. Hinnebusch, C. J., D. M. Nikolai, and D. A. Bruckner. 1991. Comparison of API Rapid STREP, Baxter Microscan Rapid Pos ID panel, BBL Minitek Differential Identification system, IDS RapID STR system, and Vitek GPI to conventional biochemical tests for identification of viridans streptococci. Am. J. Clin. Pathol. 96:459–463.
17. Kawamura, Y., X. G. Hou, F. Sultana, H. Miura, and T. Ezaki. 1995. Determination of 16S rRNA sequences of *Streptococcus mitis* and *Streptococcus gordonii* and phylogenetic relationships among members of the genus Streptococcus. Int. J. Syst. Bacteriol. 45:406–408.
18. Kikuchi, K., T. Enari, K. I. Totsuka, and K. Shimizu. 1995. Comparison of phenotypic characteristics, DNA—DNA hybridization results, and results with a commercial rapid biochemical and enzymatic reaction system for identification of viridans group streptococci. J. Clin. Microbiol. 33:1215–1222.
19. Kilian, M., L. Mikkelsen, and J. Henrichsen. 1989. Taxonomic study of viridans streptococci: description of *Streptococcus gordonii* sp. *nov.* and emended descriptions of *Streptococcus sanguis* (White and Niven 1946), *Streptococcus oralis* (Bridge and Sneath 1982), and *Streptococcus mitis* (Andrewes and Horder 1906). Int. J. Syst. Bacteriol. 39:471–484.
20. Mullis, K. B., and F. A. Faloona. 1987. Specific synthesis of DNA in vitro via a polymerase chain reaction. Methods Enzymol. 155:335–350.
21. Oyofo, B. A., S. A. Thornton, D. H. Burr, T. J. Trust, O. R. Pavlovskis, and P. Guerry. 1992. Specific detection of *Campylobacter jejuni* and *Campylobacter coli* by using polymerase chain reaction. J. Clin. Microbiol. 30:2613–2619.
22. Robinson, A. C., D. J. Kenan, J. Sweeney, and W. D. Donachie. 1986. Further evidence for overlapping transcriptional units in an *Escherichia coli* cell envelope-cell division gene cluster: DNA sequence and transcriptional organization of the ddl ftsQ region. J. Bacteriol. 167:809–817.
23. Rosa, P. A., and T. G. Schwan. 1989. A specific and sensitive assay for the lyme disease spirochete *Borrelia bugdorferi* using the polymerase chain reaction. J. Infect. Dis. 160:1018–1029.
24. Sanger, F., S. Nicklen, and A. R. Coulson. 1977. DNA sequencing with chain-terminating inhibitors. Proc. Natl. Acad. Sci. USA 74:5463–5467.
25. Tardif, G., M. C. Sulavik, G. W. Jones, and D. B. Clewell. 1989. Spontaneous switching of the sucrose-promoted colony phenotype in *Streptococcus sanguis*. Infect. Immun. 57:3945–3948.
26. Walsh, C. T. 1989. Enzymes in the D-alanine branch of bacterial cell wall peptidoglycan assembly. J. Biol. Chem. 264:2393–2396.
27. Whiley, R. A. and J. M. Hardie. 1988. *Streptococcus vestibularis* sp. *nov.* from the human oral cavity. Int. J. Syst. Bacteriol. 38:335–339.
28. Zawadzke, L. E., T. D. H. Bugg, and C. T. Walsh. 1991. Existence of two D-alanine:D-alanine ligases in *Escherichia coli*: cloning and sequencing of the ddlA gene, and purification and characterization of the DdlA and DdlB enzymes. Biochemistry 30:1673–1682.

What is claimed is:

1. A purified polynucleotide that hybridizes under stringent conditions with a nucleic acid encoding a D-alanine:D-alanine ligase of a Streptococci species selected from the group consisting of S. gordonii, S. mitis, S. mutans, S. oralis, S. salivarius, S. sanguis, S. anginosus, S. constellatus, and S. interrmedius, wherein said purified polynucleotide consists of a nucleotide sequence that:

a) has from 12 to 1095 nucleotides;

b) is internal to a polynucleotide of a streptococci ddl gene amplified by the following degenerate pair of primers, said polynucleotide being from about 600 to about 1100 bp in length:

```
                                                              (SEQIDNO:35)
V1: 5'-GGX GAA GAT GGX TCX TTX CAA GGX-3'
         G       C      AG  C       G
                               A (SEQIDNO:36)
V2: 3'-TTA TGI TAI GGI CCI AAA TG-5'
         G    A              G
              G;
``` wherein X represents A, T, G, or C and I represents inosine; and c) does not hybridize with a genome of a Streptococcus strain belonging to another species under said stringent hybridization conditions.

2. A purified polynucleotide according to claim 1, wherein said purified polynucleotide is selected from the group consisting of:

a) 5'-GTCGAAGGTGATGATATGAC-3' (SEQ ID N°1);
b) 3'-GACAGTACGCAGTCTTACGTC-5' (SEQ ID N°2);
c) 5'-ATTGAAGGCGAGCCTTTAGAAAG-3' (SEQ ID N°3);
d) 3'-CTAGGACAATAGCAAC-5' (SEQ ID N°4);
e) 5'-TGCAGAAGTAGAGGCAAATC-3' (SEQ ID N°5);
f) 3'-TTCCTCGGTTTTCGTCAACCG-5' (SEQ ID N°6);
g) 5'-GCAGCAGTAGCAGAGACGCT-3' (SEQ ID N°7);
h) 3'-CACGGACGTCTTCAGTACTG-5' (SEQ ID N°8);
i) 5'-GTCGATGGCGAGGATCTAGAGC-3' (SEQ ID N°9);
j) 3'-TGCCGAGCGCTCTAACTCCA-5' (SEQ ID N°10);
k) 5'-TGAAATCGAGGTTGGCCTAC-3' (SEQ ID N°11);
l) 3'-TTCCC(G/T)CTCTAAAAGGATTTGC-5' (SEQ ID N°12);
m) 5'-CTTATGTCGGCTGCAATATCC-3' (SEQ ID N°13);
n) 5'-GTCGATGGCGAGGATCTAGAGC-3' (SEQ ID N°14);
o) 3'-CAGAAGGTCCCCTTCAACAA-5' (SEQ ID N°15); and
p) 3'-GACTACGCAGTTTTACGTCTC-5' (SEQ ID N°16).

3. A pair of purified oligonucleotides capable of amplifying specifically a polynucleotide internal to the ddl gene of a given species belonging to the Streptococci genus, wherein said species is selected from the group consisting of *S. gaordonii, S. mitis, S. mutans, S. oralis, S. salivarius*, and *S. sanguis*, and wherein said pair of purified oligonucleotides is selected from the group consisting of:

a) 5'-GTCGAAGGTGATGATATGAC-3' (SEQ ID N°1)
3'-GACAGTACGCAGTCTTACGTC-5' (SEQ ID N°2);
b) 5'-ATTGAAGGCGAGCCTTTAGAAAG-3' (SEQ ID N°3)
3'-CTAGGACAATAGCAAC-5' (SEQ ID N°4);
c) 5'-GCAGCAGTAGCAGAGACGCT-3' (SEQ ID N°7)
3'-CACGGACGTCTTCAGTACTG-5' (SEQ ID N°8);
d) 5'-GTCGATGGCGAGGATCTAGAGC-3' (SEQ ID N°9)
3'-TGCCGAGCGCTCTAACTCCA-5' (SEQ ID N°10);
e) 5'-TGCAGAAGTAGAGGCAAATC-3' (SEQ ID N°5)
3'-TTCCTCGGTTTTCGTCAACCG-5' (SEQ ID N°6);
f) 5'-TGAAATCGAGGTTGGCCTAC-3' (SEQ ID N°11)
3'-TTCCC(G/T)CTCTAAAAGGATTTGC-5' (SEQ ID N°12);
g) 5'-CTTATGTCGGCTGCAATATCC-3' (SEQ ID N°13)
3'-TTCCC(G/T)CTCTAAAAGGATTTGC-5' (SEQ ID N°12);
h) 5'-GTCGATGGCGAGGATCTAGAGC-3' (SEQ ID N°14)
3'-CAGAAGGTCCCCTTCAACAA-5' (SEQ ID N°15); and
i) 5'-GTCGATGGCGAGGATCTAGAGC-3' (SEQ ID N°14)
3'-GACTACGCAGTTTTACGTCTC-5' (SEQ ID N°16).

4. A polynucleotide according to claim 1, wherein said polynucleotide is selected from the group consisting of:

a) SEQ ID No. 17;
b) a polynucleotide having from 12 to 591 consecutive nucleotides of SEQ ID No. 17; and
c) a polynucleotide having from 12 to 591 consecutive nucleotides of a sequence fully complementary of SEQ ID No. 17.

5. A recombinant vector comprising a polynucleotide according to claim 4.

6. The recombinant vector of claim 5, which is the plasmid pAT 439 contained in the *E. coli* strain deposited under Accession No. I-1855.

7. A polynucleotide according to claim 1, wherein said polynucleotide is selected from the group consisting of:

a) SEQ ID No. 18;
b) a polynucleotide having from 12 to 594 consecutive nucleotides of SEQ ID No. 18; and
c) a polynucleotide having from 12 to 594 consecutive nucleotides of a sequence fully complementary of SEQ ID No. 18.

8. A recombinant vector comprising a polynucleotide according to claim 7.

9. The recombinant vector of claim 8, which is the plasmid pAT 440 contained in the *E. coil* strain deposited under Accession No. I-1856.

10. A polynucleotide according to claim 1, wherein said polynucleotide is selected from the group consisting of:

a) SEQ ID No. 19;
b) a polynucleotide having from 12 to 591 consecutive nucleotides of SEQ ID No. 19; and
c) a polynucleotide having from 12 to 591 consecutive nucleotides of a sequence fully complementary of SEQ ID No. 19.

11. A recombinant vector comprising a polynucleotide according to claim 10.

12. The recombinant vector of claim 11, which is the plasmid pAT 441 contained in the *E. coli* strain deposited under Accession No. I-1857.

13. A polynucleotide according to claim 1, wherein said polynucleotide is selected from the group consisting of:

a) SEQ ID No. 20;
b) a polynucleotide having from 12 to 591 consecutive nucleotides of SEQ ID No. 20; and
c) a polynucleotide having from 12 to 591 consecutive nucleotides of a sequence fully complementary of SEQ ID No. 20.

14. A recombinant vector comprising a polynucleotide according to claim 13.

15. The recombinant vector of claim 14, which is the plasmid pAT 442 contained in the *E. coli* strain deposited under Accession No. I-1858.

16. A polynucleotide according to claim 1, wherein said polynucleotide is selected from the group consisting of:

a) SEQ ID No. 21;
b) a polynucleotide having from 12 to 591 consecutive nucleotides of SEQ ID No. 21; and
c) a polynucleotide having from 12 to 591 consecutive nucleotides of a sequence fully complementary of SEQ ID No. 21.

17. A recombinant vector comprising a polynucleotide according to claim 16.

18. The recombinant vector of claim 17, which is the plasmid pAT 438 contained in the *E. coli* strain deposited under Accession No. I-1854.

19. A polynucleotide according to claim 1, wherein said polynucleotide is selected from the group consisting of:

a) SEQ ID No. 22;

b) a polynucleotide having from 12 to 591 consecutive nucleotides of SEQ ID No. 22; and c) a polynucleotide having from 12 to 591 consecutive nucleotides of a sequence fully complementary of SEQ ID No. 22.

20. A recombinant vector comprising a polynucleotide according to claim 19.

21. The recombinant vector of claim 20, which is the plasmid pAT 443 contained in the *E. coli* strain deposited under Accession No. I-1859.

22. A polynucleotide according to claim 1, wherein said polynucleotide is selected from the group consisting of:

a) SEQ ID No. 23;

b) a polynucleotide having from 12 to 591 consecutive nucleotides of SEQ ID No. 23; and c) a polynucleotide having from 12 to 591 consecutive nucleotides of a sequence fully complementary of SEQ ID No. 23.

23. A recombinant vector comprising a polynucleotide according to claim 22.

24. The recombinant vector of claim 23, which is the plasmid pAT 444 contained in the *E. coli* strain deposited under Accession No. I-1860.

25. A polynucleotide according to claim 1, wherein said polynucleotide is selected from the group consisting of:

a) SEQ ID No. 24;

b) a polynucleotide having from 12 to 591 consecutive nucleotides of SEQ ID No. 24; and c) a polynucleotide having from 12 to 591 consecutive nucleotides of a sequence fully complementary of SEQ ID No. 24.

26. A recombinant vector comprising a polynucleotide according to claim 25.

27. The recombinant vector of claim 26, which is the plasmid pAT 445 contained in the *E. coli* strain deposited under Accession No. I-1861.

28. A polynucleotide according to claim 1, wherein said polynucleotide is selected from the group consisting of:

a) SEQ ID No. 25;

b) a polynucleotide having from 12 to 591 consecutive nucleotides of SEQ ID No. 25; and c) a polynucleotide having from 12 to 591 consecutive nucleotides of a sequence fully complementary of SEQ ID No 25.

29. A recombinant vector comprising a polynucleotide according to claim 28.

30. A purified polynucleotide that hybridizes under stringent conditions with a nucleic acid encoding a D-alanine:D-alanine ligase of a Enterococci species selected from the group consisting of *E. avium, E. pseudoavium, E. cecorum, E. saccarolyticus, E. dispar,* and *E. hirae,* wherein said purified polynucleotide:

a) has from 12 to 1095 nucleotides;

b) is internal to a polynucleotide of a Enterococci ddl gene amplified by the following degenerate pair of primers, said polynucleotide being from about 600 to about 1100 bp in length:

```
                                              (SEQIDNO:35)
V1: 5'-GGX GAA GAT GGX TCX TTX CAA GGX-3'
         G         C     AG  C     G
                                   A
```

```
                                              (SEQIDNO:36)
V2: 3'-TTA TGI TAI GGI CCI AAA TG-5'
         G    A              G
              G;
``` wherein X represents A, T, G, or C and I represents inosine; and c) does not hybridize with a genome of an Enterococcus strain belonging to another species under said stringent hybridization conditions.

31. A polynucleotide according to claim 30, wherein said polynucleotide is selected from the group consisting of:

a) SEQ ID No. 26;

b) a polynucleotide having from 12 to 600 consecutive nucleotides of SEQ ID No. 26; and c) a polynucleotide having from 12 to 600 consecutive nucleotides of a sequence fully complementary of SEQ ID No. 26.

32. A recombinant vector comprising a polynucleotide according to claim 31.

33. The recombinant vector of claim 32, which is the plasmid pAT 409 contained in an *E. coli* strain.

34. A polynucleotide according to claim 30, wherein said polynucleotide is selected from the group consisting of:

a) SEQ ID No. 27;

b) a polynucleotide having from 12 to 600 consecutive nucleotides of SEQ ID No. 27; and c) a polynucleotide having from 12 to 600 consecutive nucleotides of a sequence fully complementary of SEQ ID No. 27.

35. A recombinant vector comprising a polynucleotide according to claim 34.

36. The recombinant vector of claim 35, which is the plasmid pAT 412 contained in an *E. coli* strain.

37. A polynucleotide according to claim 30, wherein said polynucleotide is selected from the group consisting of:

a) SEQ ID No. 28;

b) a polynucleotide having from 12 to 585 consecutive nucleotides of SEQ ID No. 28; and c) a polynucleotide having from 12 to 585 consecutive nucleotides of a sequence fully complementary of SEQ ID No. 28.

38. A recombinant vector comprising a polynucleotide according to claim 37.

39. The recombinant vector of claim 38, which is the plasmid pAT 410 contained in an *E. coli* strain.

40. A polynucleotide according to claim 30, wherein said polynucleotide is selected from the group consisting of:

a) SEQ ID No. 29;

b) a polynucleotide having from 12 to 600 consecutive nucleotides of SEQ ID No. 29; and c) a polynucleotide having from 12 to 600 consecutive nucleotides of a sequence fully complementary of SEQ ID No. 29.

41. A recombinant vector comprising a polynucleotide according to claim 40.

42. The recombinant vector of claim 41, which is the plasmid pAT 413 contained in an *E. coli* strain.

43. A polynucleotide according to claim 30, wherein said polynucleotide is selected from the group consisting of:

a) SEQ ID No. 30;

b) a polynucleotide having from 12 to 600 consecutive nucleotides of SEQ ID No. 30; and c) a polynucleotide having from 12 to 600 consecutive nucleotides of a sequence fully complementary of SEQ ID No. 30.

44. A recombinant vector comprising a polynucleotide according to claim 43.

45. The recombinant vector of claim 44, which is the plasmid pAT 411 contained in an *E. coli* strain.

46. A polynucleotide according to claim 30, wherein said polynucleotide is selected from the group consisting of:
   a) SEQ ID No. 31;
   b) a polynucleotide having from 12 to 1095 consecutive nucleotides of SEQ ID No. 31; and
   c) a polynucleotide having from 12 to 1095 consecutive nucleotides of a sequence fully complementary of SEQ ID No. 31.

47. A recombinant vector comprising a polynucleotide according to claim 46.

48. The recombinant vector of claim 47, which is the plasmid pAT 405 contained in an *E. coli* strain.

49. A purified polynucleotide selected from the group consisting of:
   a) SEQ ID No. 32;
   b) a polynucleotide having from 50 to 1001 consecutive nucleotides of SEQ ID No. 32; and
   c) a polynucleotide having a sequence fully complementary to SEQ ID No. 32 or to the polynucleotide b).

50. A recombinant vector comprising a polynucleotide according to claim 49.

51. The recombinant vector of claim 50, which is the plasmid pAT 408 contained in an *E. coli* strain.

52. A polynucleotide, wherein said polynucleotide is selected from the group consisting of:
   a) SEQ ID No. 33;
   b) a polynucleotide having from 12 to 600 consecutive nucleotides of SEQ ID No. 33; and
   c) a polynucleotide having from 12 to 600 consecutive nucleotides of a sequence fully complementary of SEQ ID No. 33.

53. A recombinant vector comprising a polynucleotide according to claim 52.

54. The recombinant vector of claim 53, which is the plasmid pAT 406 contained in an *E. coli* strain.

55. A method for detecting a bacterium belonging to the Streptococci genus or to the Enterococci genus in a biological sample comprising the steps of:
   a) bringing into contact a purified polynucleotide according to any one of claims 1, 2, 4, 7, 10, 13, 16, 19, 22, 25, 28, 31, 34, 37, 40, 43, 46, 49, or 52 with a biological sample; and
   b) detecting hybrid nucleic acid molecule formed between said purified polynucleotide and nucleic acid molecules contained in the biological sample.

56. The method of claim 55, wherein before step a), nucleic acid molecules of the biological sample have been made available to a hybridization reaction.

57. A method for detecting a bacterium belonging to the Streptococci genus or to the Enterococci genus in a biological sample comprising the steps of:
   a) bringing into contact a purified polynucleotide according to any one of claims 1, 2, 4, 7, 10, 13, 16, 19, 22, 25, 28, 31, 34, 37, 40, 43, 46, 49, or 52 that has been immobilized onto a substrate with a biological sample; and
   b) bringing into contact the hybrid nucleic acid molecule formed between said purified polynucleotide and the nucleic acid contained in the biological sample with a labeled polynucleotide according to anyone of claims 1, 2, 4, 7, 10, 13, 16, 19, 22, 25, 28, 31, 34, 37, 40, 43, 46, 49, or 52, said labeled polynucleotide having a sequence that does not overlap with the sequence of the polynucleotide of step a).

58. The method of claim 57, wherein, before step a), nucleic acid molecules of the biological sample have been made available to a hybridization reaction.

59. The method of claim 58, wherein, before step b), nucleic acid molecules that are not hybridized with the immobilized purified polynucleotide are removed.

60. A method for detecting a bacterium belonging to the Streptococci genus in a biological sample comprising the steps of:
   a) bringing into contact nucleic acid molecules contained in the biological sample with a pair of purified polynucleotides according to any one of claims 1, 2, 3, 4, 7, 10, 13, 16, 19, 22, 25, or 28;
   b) amplifying said nucleic acid molecules; and
   c) detecting nucleic acid fragments that have been amplified, for example by gel electrophoresis or with a labeled polynucleotide according to any one of claims 1, 2, 4, 7, 10, 13, 16, 19, 22, 25, or 28.

61. The method of claim 60, wherein before step a), nucleic acid molecules of the biological sample have been made available to a hybridization reaction.

62. A kit for detecting a bacterium belonging to the Streptococci genus in a biological sample comprising:
   a) a purified polynucleotide according to claim 1, 2, 4, 7, 10, 13, 16, 19, 22, 25, or 28; and
   b) reagents necessary to perform a nucleic acid hybridization reaction.

63. A kit for detecting a bacterium belonging to the Streptococci genus in a biological sample comprising:
   a) a purified polynucleotide according to claim 1, 2, 4, 7, 10, 13, 16, 19, 22, 25, or 28 that is immobilized onto a substrate;
   b) reagents necessary to perform a nucleic acid hybridization reaction; and
   c) a purified polynucleotide according to claim 1, 2, 4, 7, 10, 13, 16, 19, 22, 25, or 28, which is radioactively or non-radioactively labeled, the sequence of which does not overlap with the sequence of the polynucleotide of step a).

64. A kit for detecting a bacterium belonging to the Streptococci genus in a biological sample comprising:
   a) a pair of purified oligonucleotides according to claim 1, 2, 4, 7, 10, 13, 16, 19, 22, 25, or 28; and
   b) reagents necessary to perform a nucleic acid amplification reaction.

65. A polynucleotide comprising the full length coding sequence of a Streptococci D-Ala:D-Ala ligase containing a polynucleotide sequence according to claim 1.

66. The recombinant vector of claim 29, which is the plasmid pAT 446 contained in the *E. coli* strain deposited under Accession No. I-1862.

67. A kit for detecting a bacterium belonging to the Enterococci genus in a biological sample comprising:
   a) a purified polynucleotide according to claim 31, 34, 37, 40, 42, 46, 49, 52, or 30; and
   b) reagents necessary to perform a nucleic acid hybridization reaction.

68. A kit for detecting a bacterium belonging to the Enterococci genus in a biological sample comprising:

a) a purified polynucleotide according to claim 31, 34, 37, 40, 42, 46, 49, 52, or 30 that is immobilized onto a substrate;

b) reagents necessary to perform a nucleic acid hybridization reaction; and c) a purified polynucleotide according to claim 31, 34, 37, 40, 42, 46, 49, 52, or 30, which is radioactively or non-radioactively labeled, the sequence of which does not overlap with the sequence of the polynucleotide of step a).

69. A polynucleotide comprising the full length coding sequence of an Enterococi D-Ala:D-Ala ligase containing a polynucleotide sequence according to claim 30.

* * * * *